United States Patent
Marks et al.

(10) Patent No.: US 9,539,272 B2
(45) Date of Patent: Jan. 10, 2017

(54) HDAC 6 INHIBITOR-BASED METHODS FOR TREATING CANCER

(75) Inventors: Paul A. Marks, Washington, CT (US); Weisheng Xu, Forest Hills, NY (US); Mandana Namdar, London (GB)

(73) Assignee: SLOAN-KETTERING INSTITUTE FOR CANCER RESEARCH, New York, NY (US)

( * ) Notice: Subject to any disclaimer, the term of this patent is extended or adjusted under 35 U.S.C. 154(b) by 1237 days.

(21) Appl. No.: 13/382,336

(22) PCT Filed: Jul. 2, 2010

(86) PCT No.: PCT/US2010/040914
§ 371 (c)(1),
(2), (4) Date: Jul. 11, 2012

(87) PCT Pub. No.: WO2011/005688
PCT Pub. Date: Jan. 13, 2011

(65) Prior Publication Data
US 2012/0270818 A1    Oct. 25, 2012

Related U.S. Application Data

(60) Provisional application No. 61/223,227, filed on Jul. 6, 2009.

(51) Int. Cl.
| | | |
|---|---|---|
| *A01N 43/04* | (2006.01) | |
| *A61K 31/70* | (2006.01) | |
| *A01N 37/28* | (2006.01) | |
| *A61K 31/19* | (2006.01) | |
| *A01N 43/76* | (2006.01) | |
| *A61K 31/42* | (2006.01) | |
| *C12N 5/00* | (2006.01) | |
| *C12N 5/02* | (2006.01) | |
| *A61K 31/704* | (2006.01) | |
| *A61K 31/167* | (2006.01) | |
| *A61K 31/422* | (2006.01) | |
| *A61K 31/7048* | (2006.01) | |
| *A61K 45/06* | (2006.01) | |

(52) U.S. Cl.
CPC .......... *A61K 31/704* (2013.01); *A61K 31/167* (2013.01); *A61K 31/19* (2013.01); *A61K 31/422* (2013.01); *A61K 31/7048* (2013.01); *A61K 45/06* (2013.01)

(58) Field of Classification Search
CPC .... A61K 31/167; A61K 31/19; A61K 31/422; A61K 31/704; A61K 31/7048; A61K 45/06; A61K 2300/00
USPC ...................... 514/27, 575, 34, 376; 435/375
See application file for complete search history.

(56) References Cited

U.S. PATENT DOCUMENTS

2006/0239909 A1* 10/2006 Anderson .............. A61K 31/35
424/1.49

FOREIGN PATENT DOCUMENTS

WO    WO 2005/023179    3/2005

OTHER PUBLICATIONS

Definition of "Cancer" by MedicineNet.com. (2004) Retrieved on Sep. 16, 2005. Retrieved from the internet at <http://www.medterms.com>.*
"Metastasis." Encyclopedia Britannica. Encyclopdia Britannica Online Academic Edition. Encyclopedia Britannica Inc., 2011. Web. Dec. 6, 2011. <http://www.britannica.com/EBchecked/topic/378021/metastasis>.*
Search Report dated Nov. 28, 2012 issued in the corresponding European Patent Application No. 10 79 7676.
Kozikowski et al.: "Use of the Nitrile Oxide Cycloaddition (NOC) Reaction for Molecular Probe Generation: A New Class of Enzyme Selective Histone Deacetylase Inhibitors (HDACIs) Showing Picomolar Activity at HDAC6", Journal of Medicinal Chemistry, vol. 51, No. 15, Aug. 1, 2008 (pp. 4370-4373).

* cited by examiner

*Primary Examiner* — Scarlett Goon
(74) *Attorney, Agent, or Firm* — Baker Botts L.L.P.

(57) ABSTRACT

This invention provides methods for treating a subject afflicted with cancer, comprising concurrently administering (i) an HDAC 6-selective inhibitor and (ii) a suitable cytotoxic agent such as SAHA, doxorubicin or etoposide. This invention also provides methods for inducing the death of a transformed cell such as a cancer cell, comprising concurrently contacting the cell with (i) an HDAC 6-selective inhibitor and (ii) a suitable cytotoxic agent such as SAHA, doxorubicin or etoposide.

14 Claims, 26 Drawing Sheets

Downregulation of HDAC6 expression show a modest decrease in cell growth and no effect on cell viability

HDAC 6 INHIBITOR-BASED METHODS FOR TREATING CANCER

This application is the U.S. national phase of PCT/US2010/040914, filed Jul. 2, 2010, which claims priority from U.S. Provisional Application No. 61/223,227, filed Jul. 6, 2009, the contents of both of which are incorporated herein by reference.

This invention was made with government support under grant P30CA08748-44 from the National Institutes of Health. Accordingly, the U.S. Government has certain rights in the invention.

Throughout this application, various publications are cited. The disclosure of these publications is hereby incorporated by reference into this application to describe more fully the state of the art to which this invention pertains.

BACKGROUND OF THE INVENTION

Histone acetylation is a reversible process whereby histone and non-histone protein acetyl-transferases transfer the acetyl moiety from acetyl co-enzyme A to lysines and histone deacetylases (HDACs) remove the acetyl groups establishing the positive charge in the proteins. There are eighteen HDACs in humans of which eleven are zinc-dependent designated class I (HDACs 1, 2, 3, 8), Class IIa (HDACs 4, 5, 7, 9), Class IIb (HDACs 6, 10), and Class IV (HDAC 11) (Marks & Xu *J Cell Biochemistry* E-pubmed, 2009) (Table 1). Among the zinc-dependent HDACs, class I HDACs are primarily localized in the nucleus while class II HDACs are primarily cytoplasmic in location but shuttle between the nucleus and the cytoplasm (see reviews: Bolden et al. *Nat Rev Drug Discovery* 5:769-84, 2006; Glozak & Seto *Oncogene* 26:5420-32, 2007; Dokmanovic et al. *Mol Cancer Research* 5:981-989, 2007; Marks & Xu *J Cell Biochemisty* E-pubmed, 2009). The accumulating evidence indicates that these HDAC enzymes are not redundant in their biological activity.

In addition to histones, HDACs have many non-histone protein substrates that have a role in regulation of gene expression, cell proliferation, cell migration, cell death and angiogenesis. HDAC inhibitors cause the accumulation of acetylated forms of protein substrates and alter the structure and function of these proteins. HDAC inhibitors can induce different phenotypes in various transformed cells including growth arrest, apoptosis, reactive oxygen species-facilitated cell death and mitotic cell death. Normal cells are relatively resistant to HDAC inhibitor-induced cell death.

Among the eleven zinc-dependent HDACs, HDAC 6 is unique. HDAC 6 has two identical catalytic sites, a ubiquitin-binding site toward its C-terminal end and is primarily cytoplasmic in location. HDAC 6 is a known specific deacetylase of several proteins including α-tubulin, cortactin, peroxiredoxins, chaperone proteins, HSP90, β-Catenin, hypoxia inducible factor-1α (HIF-1α) and other proteins, but not histones in viva (see above cited reviews, and Blackwell et al., *Life Science* 82:1050-1058, 2008; Shnakar & Sirvastava *Adv Exp Med Biol* 615:261-298, 2008). A previously unrecognized substrate of HDAC 6 was recently discovered, namely, peroxiredoxins, which are proteins critical in protecting cells from the oxidative effects of $H_2O_2$ (Parmigiani et al. *PNAS* 105:9633-9638, 2008).

Suberoylanilide hydroxamic acid (vorinostat) is an inhibitor of class I HDAC 1, 2, 3, and 8, class IIb HDACs and 10, and class IV HDAC 11 (Marks & Breslow *Nat Biotechnol* 25:84-90, 2007). Tubacin (Haggerty et al. *PNAS* 100:4389-4394, 2003) (Table 2) and compound 7 (in Kozikowski et al. *J. Med Chem* 51:4370-4373, 2008) are selective HDAC 6 inhibitors as indicated by assays with purified recombinant zinc-dependent HDACs including HDAC 6 and HDAC 1.

Compound 7 is designated herein as BAHA (Table 2). As indicated above, HDAC 6 selectively deacetylates a number of proteins that have a role in regulating cell proliferation, cell migration, cell death and angiogenesis. Inhibition of HDAC 6 causes accumulation of acetylated forms of these proteins, altering their structure and function that can cause inhibition of cell proliferation, cell migration and metastasis and angiogenesis.

SUMMARY OF THE INVENTION

This invention provides a method for treating a subject afflicted with cancer, comprising concurrently administering to the subject (i) an HDAC 6-selective inhibitor and (ii) a cytotoxic agent, wherein the cytotoxic agent is not a microtubule-stabilizing agent or a proteasome inhibitor, and wherein the amounts of the HDAC 6-selective inhibitor and cytotoxic agent, when concurrently administered, are therapeutically effective.

This invention also provides a method for treating a subject afflicted with cancer, comprising concurrently administering to the subject (a) an HDAC 6-selective inhibitor and (b) a cytotoxic agent selected from the group consisting of (i) SAHA or an agent having the same mode of action, (ii) doxorubicin or an agent having the same mode of action, and (iii) etoposide or an agent having the same mode of action, wherein the amounts of HDAC 6-selective inhibitor and cytotoxic agent, when concurrently administered, are therapeutically effective.

This invention still further provides a method for inducing the death of a transformed cell, comprising concurrently contacting the cell with (i) an HDAC 6-selective inhibitor and (ii) a cytotoxic agent, wherein the cytotoxic agent is not a microtubule-stabilizing agent or a proteasome inhibitor, and wherein the amounts of the HDAC 6-selective inhibitor and cytotoxic agent, when concurrently contacted with the cell, are effective to induce the cell's death.

Finally, this invention provides a method for inducing the death of a transformed cell, comprising concurrently contacting the cell with (a) an HDAC 6-selective inhibitor and (b) a cytotoxic agent selected from the group consisting of (i) SAHA or an agent having the same mode of action, (ii) doxorubicin or an agent having the same mode of action, and (iii) etoposide or an agent having the same mode of action, and wherein the amounts of the HDAC 6-selective inhibitor and cytotoxic agent, when concurrently contacted with the cell, are effective to induce the cell's death.

DETAILED DESCRIPTION OF THE INVENTION

Terms

Figure 1:
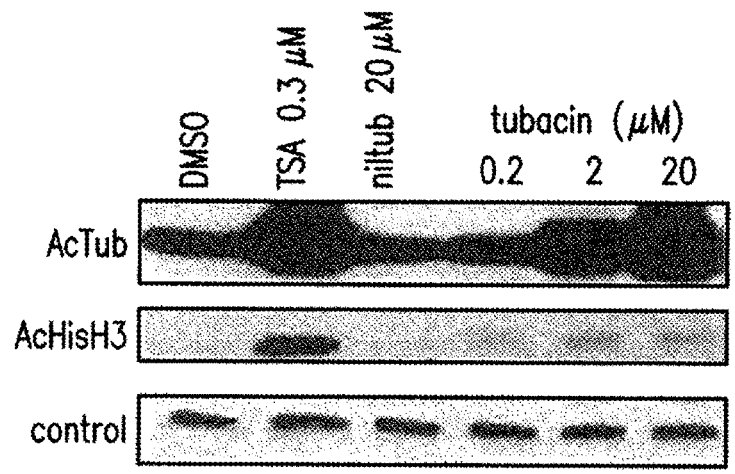
FIG. 1 Characterization of tubacin as an inhibitor of HDAC 6. Tubacin-induced accumulation of acetylated tubulin (AcTub) but not histone H3 (AcHis H3) in A549, human lung carcinoma cells, cultured for 24 hrs. (From Haggarty et al., *PNAS* 100:4389-4394, 2003). Control, dimethyl sulfoxide (DMSO) or nil-tubacin did not induce accumulation of acetylated tubacin or acetylated histones. Trichostatin A (TSA), an inhibitor of HDACs 1, 2, 3, and 6, induced accumulation of acetylated tubulin and acetylated histone H3. "Control" is alpha-tubulin for loading.

In this application, certain terms are used which shall have the meanings set forth as follows.

As used herein, "cancer" includes, without limitation, the following: acute lymphoblastic leukemia; acute myeloid leukemia; adrenocortical carcinoma; AIDS-related cancers; AIDS-related lymphoma; anal cancer; appendix cancer; astrocytoma, childhood cerebellar or cerebral; basal cell carcinoma; bile duct cancer, extrahepatic; bladder cancer; bone cancer, osteosarcoma/malignant fibrous histiocytoma; brainstem glioma; brain tumor; cerebellar astrocytoma; cerebral astrocytoma/malignant glioma; ependymoma; medulloblastoma; supratentorial primitive neuroectodermal tumors; visual pathway and hypothalamic glioma; breast cancer; bronchial adenomas/carcinoids; burkitt lymphoma; carcinoid tumor, childhood; carcinoid tumor, gastrointestinal; carcinoma of unknown primary; central nervous system lymphoma, primary; cerebellar astrocytoma, childhood; cerebral astrocytoma/malignant glioma, childhood; cervical cancer; childhood cancers; chronic lymphocytic leukemia; chronic myelogenous leukemia; chronic myeloproliferative disorders; colon cancer; cutaneous T-cell lymphoma; desmoplastic small round cell tumor; endometrial cancer; ependymoma; esophageal cancer; Ewing's sarcoma in the Ewing family of tumors; extracranial germ cell tumor, childhood; extragonadal germ cell tumor; extrahepatic bile duct cancer; eye cancer, intraocular melanoma; eye cancer, retinoblastoma; gallbladder cancer; gastric (stomach) cancer; gastric (stomach) cancer, childhood; gastrointestinal carcinoid tumor; gastrointestinal stromal tumor (GIST); germ cell tumor, extracranial, childhood; germ cell tumor, extragonadal; germ cell tumor, ovarian; gestational trophoblastic tumor; glioma, adult; glioma, childhood brain stem; glioma, childhood cerebral astrocytoma; glioma, childhood visual pathway and hypothalamic; gastric carcinoid; hairy cell leukemia; head and neck cancer; hepatocellular (liver) cancer; Hodgkin lymphoma; hypopharyngeal cancer; hypothalamic and visual pathway glioma, childhood; intraocular melanoma; islet cell carcinoma (endocrine pancreas); Kaposi sarcoma; kidney cancer (renal cell cancer); laryngeal cancer; leukemias; leukemia, acute lymphoblastic (also called acute lymphocytic leukemia); leukemia, acute myeloid (also called acute myelogenous leukemia); leukemia, chronic lymphocytic (also called chronic lymphocytic leukemia); leukemia, chronic myelogenous (also called chronic myeloid leukemia); leukemia, hairy cell; lip and oral cavity cancer; liver cancer (primary); lung cancer, non-small cell; lung cancer, small cell; lymphomas; lymphoma, AIDS-related; lymphoma, Burkitt; lymphoma, cutaneous T-cell; lymphoma, Hodgkin; lymphomas, non-Hodgkin (an old classification of all lymphomas except Hodgkin's); lymphoma, primary central nervous system; macroglobulinemia, Waldenström; malignant fibrous histiocytoma of bone/osteosarcoma; medulloblastoma, childhood; melanoma; melanoma, intraocular (eye); Merkel cell carcinoma; mesothelioma, adult malignant; mesothelioma, childhood; metastatic squamous neck cancer with occult primary; mouth cancer; multiple endocrine neoplasia syndrome, childhood; multiple myeloma/plasma cell neoplasm; mycosis fungoides; myelodysplastic syndromes; myelodysplastic/myeloproliferative diseases; myelogenous leukemia, chronic; myeloid leukemia, adult acute; myeloid leukemia, childhood acute; myeloma, multiple (cancer of the bone-marrow); myeloproliferative disorders, chronic; nasal cavity and paranasal sinus cancer; nasopharyngeal carcinoma; neuroblastoma; non-Hodgkin lymphoma; non-small cell lung cancer; oral cancer; oropharyngeal cancer; osteosarcoma/malignant fibrous histiocytoma of bone; ovarian cancer; ovarian epithelial cancer (surface epithelial-stromal tumor); ovarian germ cell tumor; ovarian low malignant potential tumor; pancreatic cancer; pancreatic cancer, islet cell; paranasal sinus and nasal cavity cancer; parathyroid cancer; penile cancer; pharyngeal cancer; pheochromocytoma; pineal astrocytoma; pineal germinoma; pineoblastoma and supratentorial primitive neuroectodermal tumors, childhood; pituitary adenoma; plasma cell neoplasia/multiple myeloma; pleuropulmonary blastoma; primary central nervous system lymphoma; prostate cancer; rectal cancer; renal cell carcinoma (kidney cancer); renal pelvis and ureter, transitional cell cancer; retinoblastoma; rhabdomyosarcoma, childhood; salivary gland cancer; sarcoma, Ewing family of tumors; sarcoma, Kaposi; sarcoma, soft tissue; sarcoma, uterine; Sézary syndrome; skin cancer (nonmelanoma); skin cancer (melanoma); skin carcinoma, Merkel cell; small cell lung cancer; small intestine cancer; soft tissue sarcoma; squamous cell carcinoma; squamous neck cancer with occult primary, metastatic; stomach cancer; supratentorial primitive neuroectodermal tumor, childhood; T-cell lymphoma, cutaneous; testicular cancer; throat cancer; thymoma, childhood; thymoma and thymic carcinoma; thyroid cancer; thyroid cancer, childhood; transitional cell cancer of the renal pelvis and ureter; trophoblastic tumor, gestational; unknown primary site, carcinoma of, adult; unknown primary site, cancer of, childhood; ureter and renal pelvis, transitional cell cancer; urethral cancer; uterine cancer, endometrial; uterine sarcoma; vaginal cancer; visual pathway and hypothalamic glioma, childhood; vulvar cancer; Waldenström macroglobulinemia; and Wilms tumor (kidney cancer), childhood.

As used herein, "concurrently administering" a first and second agent to a subject means administering the first agent according to a first regimen, and administering the second agent according to a second regimen, whereby the first and second regimens overlap in time. For example, a first and second agent are concurrently administered to a subject if, beginning on the first day of treatment, the first agent is administered once per week for 10 weeks, and the second agent is administered daily for the first, third, fifth and seventh weeks.

As used herein, "cytotoxic agent" shall mean an agent that, when present in, on and/or in proximity with a cell, causes that cell's death directly and/or indirectly. Cytotoxic agents include, for example, small molecules as well as peptides and nucleic acids.

As used herein, two cytotoxic agents have the "same mode of action" if they act to kill a cell via the same biochemical mechanism or plurality of mechanisms. For example, two cytotoxic agents have the same mode of action if they both act to kill a cell via DNA intercalation.

As used herein, "HDAC 6-selective inhibitor" shall mean an agent that inhibits HDAC 6 more than it inhibits any other HDAC. In one embodiment, the HDAC 6-selective inhibitor inhibits HDAC 6 at least two-fold more than it inhibits any other HDAC. In another embodiment, the HDAC 6-selective inhibitor inhibits HDAC 6 at least 10-fold more than it inhibits any other HDAC. In a third embodiment, the HDAC 6-selective inhibitor inhibits HDAC 6 more than it inhibits any other enzyme.

"Pharmaceutically acceptable carriers" are well known to those skilled in the art and include, but are not limited to, 0.01-0.1 M and preferably 0.05 M phosphate buffer or 0.8% saline. Additionally, such pharmaceutically acceptable carriers can be aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions and suspensions, including saline and buffered media. Parenteral vehicles include sodium chloride solution, Ringer's dextrose, dextrose and sodium chloride, lactated Ringer's and fixed oils. Intravenous vehicles include fluid and nutrient replenishers, electrolyte replenishers such as Ringer's dextrose, those based on Ringer's dextrose, and the like. Fluids used commonly for i.v. administration are found, for example, in *Remington: The Science and Practice of Pharmacy*, 20$^{th}$ Ed., p. 808, Lippincott Williams & Wilkins (2000). Preservatives and other additives may also be present, such as, for example, antimicrobials, antioxidants, chelating agents, inert gases, and the like.

As used herein, "subject" shall mean any animal, such as a human, non-human primate, mouse, rat, guinea pig or rabbit.

As used herein, "treating" a subject afflicted with a disorder shall mean slowing, stopping or reversing the disorder's progression. In the preferred embodiment, treating a subject afflicted with a disorder means reversing the disorder's progression, ideally to the point of eliminating the disorder itself.

Embodiments of the Invention

In the present invention, it has now been found that HDAC 6-selective inhibitors markedly increase the sensitivity of transformed, but not normal cells, to cytotoxic drugs. This discovery has important therapeutic significance for the treatment of cancer.

Specifically, this invention provides a method for treating a subject afflicted with cancer, comprising concurrently administering to the subject (i) an HDAC 6-selective inhibitor and (ii) a cytotoxic agent, wherein the cytotoxic agent is not a microtubule-stabilizing agent (e.g., paclitaxel) or a proteasome inhibitor (e.g., bortezomib), and wherein the amounts of the HDAC 6-selective inhibitor and cytotoxic agent, when concurrently administered, are therapeutically effective.

This invention also provides a method for treating a subject afflicted with cancer, comprising concurrently administering to the subject (a) an HDAC 6-selective inhibitor and (b) a cytotoxic agent selected from the group consisting of (i) SAHA or an agent having the same mode of action, (ii) doxorubicin or an agent having the same mode of action, and (iii) etoposide or an agent having the same mode of action, wherein the amounts of HDAC 6-selective inhibitor and cytotoxic agent, when concurrently administered, are therapeutically effective.

Preferably, in these methods, the subject is human. Also, in a preferred embodiment, the HDAC 6-selective inhibitor is tubacin or BAHA. In a further preferred embodiment, the cytotoxic agent is SAHA, doxorubicin or etoposide.

In a particularly preferred embodiment, this invention provides a method for treating a subject afflicted with cancer, comprising concurrently administering to the subject one of the following combinations of agents: (i) tubacin and SAHA; (ii) tubacin and doxorubicin; (iii) tubacin and etoposide; (iv) BAHA and SAHA; (v) BAHA and doxorubicin; and (vi) BAHA and etoposide, wherein the amounts of each agent in each combination, when concurrently administered, are therapeutically effective.

In these therapeutic methods, each agent is preferably administered as an admixture with a pharmaceutically acceptable carrier. Pharmaceutically acceptable carriers are well known in the art.

The following information exemplifies the preferred embodiments of this invention.

For the HDAC 6 inhibitors, BAHA, in one embodiment, is administered to the subject at 50-200 mg/day (e.g., 80, 90, 100, 110 or 120 mg/day) for three to four days, followed by a three to four day rest period. Ideally, this cycle of administration followed by rest is repeated multiple times (e.g. 10 times) or indefinitely.

Likewise, in another embodiment, tubacin is administered to the subject at 50-200 mg/day (e.g., 80, 90, 100, 110 or 120 mg/day) for three to four days, followed by a three to four day rest period. Ideally, this cycle of administration followed by rest is repeated multiple times (e.g. 10 times) or indefinitely.

RUBEX® (doxorubicin hydrochloride) for injection has been used successfully to produce regression in disseminated neoplastic conditions such as acute lymphoblastic leukemia, acute myeloblastic leukemia, Wilms' tumor, neuroblastoma, soft tissue and bone sarcomas, breast carcinoma, ovarian carcinoma, transitional cell bladder carcinoma, thyroid carcinoma, gastric carcinoma, Hodgkin's disease, malignant lymphoma and bronchogenic carcinoma in which the small cell histologic type is the most responsive compared to other cell types. The most commonly used dose schedule when doxorubicin is used as a single agent is 60 to 75 mg/m$^2$ as a single intravenous injection administered at 21-day intervals. The lower dosage should be given to patients with inadequate marrow reserves due to old age, or prior therapy, or neoplastic marrow infiltration. When used together with either BAHA or tubacin in the instant therapeutic methods, the doxorubicin dosage—rather than 60 to 75 mg/m$^2$—is preferably below 60 mg/m$^2$ (e.g., 20, 25, 30, 35, 40, 45, 50 or 55 mg/m$^2$) given as a single intravenous injection every 21 to 28 days.

Etoposide is indicated for the treatment of refractory testicular tumors and small cell lung carcinoma. It is used to treat other malignancies such as lymphoma, non-lymphocytic leukemia, and glioblastoma multiforme. The usual dosage of injectable etoposide for testicular cancer, in combination with other chemotherapeutic agents, ranges from 50 to 100 mg/m$^2$/day on days 1 through 5, to 100 mg/m$^2$/day on days 1, 3 and 5. When used together with either BAHA or tubacin in the instant therapeutic methods, the etoposide dosage is preferably below 50 mg/m$^2$/day (e.g., 20, 25, 30, 35, 40 or 45 mg/m$^2$/day) on days 1 through 5. In small cell lung carcinoma, the dosage of injectable etoposide, in combination with other chemotherapeutic agents, ranges from 35 mg/m$^2$/day for four days to 50 mg/m$^2$/day for five days. When used together with either BAHA or tubacin in the instant therapeutic methods, the etoposide dosage is preferably below 35 mg/m$^2$/day (e.g., 10, 15, 20, 25 or 30 mg/m$^2$/day) for four days. Chemotherapy courses are repeated at three to four-week intervals after adequate recovery from any toxicity.

ZOLINZA® (vorinostat, i.e., SAHA) is indicated for the treatment of cutaneous manifestations in patients with cutaneous T-cell lymphoma who have progressive, persistent or recurrent disease on or following two systemic therapies. The recommended dose is 400 mg orally once daily with food. When used together with either BAHA or tubacin in the instant therapeutic methods, the SAHA dosage is preferably below 400 mg/day (e.g., 100, 150, 200, 250, 300 or 350 mg/day). Treatment may be continued as long as there is no evidence of progressive disease or unacceptable toxicity.

The above dosing regimens are envisioned as being carried out concurrently, per the claimed methods. For example, in one embodiment, BAHA and doxorubicin are administered concurrently as follows: (i) BAHA is administered at 100 mg/day for multiple cycles of three to four days, followed by a three to four day rest period, while at the same time, (ii) doxorubicin is administered at below 60 mg/m² as a single intravenous injection at 21-day intervals.

This invention still further provides a method for inducing the death of a transformed cell, comprising concurrently contacting the cell (in vivo or in vitro) with (i) an HDAC 6-selective inhibitor and (ii) a cytotoxic agent, wherein the cytotoxic agent is not a microtubule-stabilizing agent or a proteasome inhibitor, and wherein the amounts of the HDAC 6-selective inhibitor and cytotoxic agent, when concurrently contacted with the cell, are effective to induce the cell's death.

This invention also provides a method for inducing the death of a transformed cell, comprising concurrently contacting the cell (in viva or in vitro) with (a) an HDAC 6-selective inhibitor and (b) a cytotoxic agent selected from the group consisting of (i) SAHA or an agent having the same mode of action, (ii) doxorubicin or an agent having the same mode of action, and (iii) etoposide or an agent having the same mode of action, and wherein the amounts of the HDAC 6-selective inhibitor and cytotoxic agent, when concurrently contacted with the cell, are effective to induce the cell's death.

Preferably, in these methods, the transformed cell is a human cell, and ideally a cancer cell. As with the instant therapeutic methods, in a preferred embodiment, the HDAC 6-selective inhibitor is tubacin or BAHA, and the cytotoxic agent is SAHA, doxorubicin or etoposide.

This invention still further provides a method for inducing the death of a transformed cell, comprising concurrently contacting the cell (in vivo or in vitro) with one of the following combinations of agents: (i) tubacin and SAHA; (ii) tubacin and doxorubicin; (iii) tubacin and etoposide; (iv) BAHA and SAHA; (v) BAHA and doxorubicin; and (vi) BAHA and etoposide, wherein the amounts of each agent in each combination, when concurrently contacted with the cell, are effective to induce the cell's death.

This invention further provides a method for treating a subject afflicted with cancer, comprising concurrently administering to the subject (i) an HDAC 6-selective inhibitor and (ii) a cytotoxic agent, wherein the cytotoxic agent acts to damage DNA, and wherein the amounts of the HDAC 6-selective inhibitor and cytotoxic agent, when concurrently administered, are therapeutically effective.

This invention still further provides a method for inducing the death of a transformed cell, comprising concurrently contacting the cell with (i) an HDAC 6-selective inhibitor and (ii) a cytotoxic agent, wherein the cytotoxic agent acts to damage DNA, and wherein the amounts of the HDAC 6-selective inhibitor and cytotoxic agent, when concurrently contacted with the cell, are effective to induce the cell's death.

DNA damage can occur, for example, via DNA intercalation or strand breakage (e.g., double strand breakage).

Finally, this invention provides kits for practicing the instant methods. For example, this invention provides a kit for use in treating a subject afflicted with cancer comprising, in separate compartments and with appropriate instructions for use, (i) an HDAC 6-selective inhibitor and (ii) a cytotoxic agent, wherein the cytotoxic agent is not a microtubule-stabilizing agent or a proteasome inhibitor, and wherein the amounts of the HDAC 6-selective inhibitor and cytotoxic agent, when concurrently administered, are therapeutically effective. Also envisioned are kits for practicing each of the other subject methods, wherein each kit comprises (in separate compartments and with appropriate instructions for use) the agents recited for its corresponding method. Likewise, the various embodiments set forth for each of the subject methods apply, mutatis mutandis, to its respective kit.

This invention will be better understood by reference to the Experimental Details which follow, but those skilled in the art will readily appreciate that the specific experiments detailed are only illustrative of the invention as described more fully in the claims which follow thereafter.

Experimental Details

Part A

I. Methods and Materials

In Vitro HDAC Assays.

HDAC inhibitors: Tubacin (Haggarty et al., 2003); HDAC inhibitor 7 (BAHA) (Kozikowski J Med Chem 51:4370-4373, 2008) and Suberoylanilide Hydroxamic Acid (SAHA, vorinostat) (Marks & Breslow Nat Biotechnol 25:84-90, 2007) (Table 2). Inhibition of HDAC 1 and HDAC 6 were analyzed with a fluorogenic substrate according to manufacture's protocol (HDAC assay reagents were purchased from BPS Biosciences, San Diego, Calif.). 50 µl reaction mixture, which contains 1×HDAC assay buffer, 5 units of recombinant human HDAC1 or HDAC 6, 10 µM substrate 3 and 1 µl inhibitor in DMSO, was incubated at 37° C. for 1 hour. The concentrations of inhibitors tested were 0.1, 1, 10, 100, 1000, 10000 and 100000 nMole/L. 1 µl inhibitor in DMSO. DMSO alone was used as control. SAHA was used as positive control, as a known HDAC inhibitor of HDAC 1 and HDAC 6. 50 µl 2× developer was added and incubated for 15 minutes at room temperature. The fluorescence intensity was measured at excitation of 360 nm and emission of 460 nm with SpectraMax Gemini XS microplate reader (Molecular Devices, Sunny Calif.).

Cell Culture and Reagents.

All Cell lines were maintained at 37° C. in water-saturated 5% $CO_2$. LNCaP human prostate cancer cells, A549 human lung cancer cells; MCF7 breast cancer cells, HFS normal human foreskin cells, and W138, normal human embryonic fibroblast cells were obtained from American Tissue Culture Collection (Manassas, Va.) or American Type Culture Collection (Rockville Md.). LNCaP cells were cultured in RPMI medium 1640, A549 in F-12 medium, MCF7, HFS and WI38 in MEM, each supplemented with 10% fetal bovine serum. Doxorubicin and Etoposide (VP-16) were purchased from Sigma. Tubacin, BAHA and SAHA were obtained privately.

Cell Growth and Viability.

$5×10^4$ cells were seeded per well in a 24-well plate and cultured overnight prior to treating with the compound and/or other agents as indicated for each study. Cells were harvested at 24, 48 and 72 hrs after treatment by trypsin digestion. Cell number and viability were determined by trypan blue exclusion (Richon et al. PNAS 93:5705-5708, 1996). At least three independent analyses were performed for each time point.

Cell Lysate Preparation and Histone Extraction.

$2×10^6$ transformed cells were cultured for 24 hrs in a 10 cm tissue culture dish with 10 ml RPMI 1640 medium. HDAC inhibitors and/or other agents were added in concentrations as indicated for each study to the cultures and cell cultured for times indicated. Cells were harvested by scrapping, washed once with PBS, lyzed with histone extraction buffer (1 ml/$10^7$ cells), which contains 10 mM $MgCl_2$, 10 mM Tris, 25 mM KCl, 1% Triton X-100, 8.6% sucrose and protease inhibitor cocktail (Roche Diagnostics Gmbh, Indianapolis, Ind.), pH 6.5. Cells were centrifuged at 600 g at 4° C. for 5 mins. The supernatants were saved as cell lyates. The pellets (nuclei) were washed once with TE buffer, suspended in 0.4 $NH_2SO_4$ (100 μl/$10^7$ cells), incubated for 1 hr on ice, and centrifuged at 10,000 g for 10 mins at 4° C. The supernatant was collected, mixed with 1 ml acetone, incubated at −20° C. for more than 1 hr, and centrifuged at 10,000 g for 10 mins at 4° C. The pellets were suspended in water (100 μl/$10^7$ cells). The protein concentrations were measured with Braford reagent (Bio-Rad, Hercules, Calif.).

Western Blotting.

$1 \times 10^6$ cells in a 10 cm diameter cell culture dish were washed with PBS, harvested by trypsinization in 0.05% trypsin for LNCaP and 0.25% trypsin for MCF7, A549, HFS and WI38 resuspended in RIPA at 50 μl for every $1 \times 10^6$ cells. Antibodies used were: anti-acetylated tubulin (Sigma), anti-HDAC 6 (Santa Cruz Biotechnology), and anti-tubulin (Calbiochem), (Xu et al. *Cancer Research*, 65:7832-7839, 2005).

II. Results

Establishing that Tubacin and BAHA are Selective Inhibitors of HDAC 6

Figure 2:
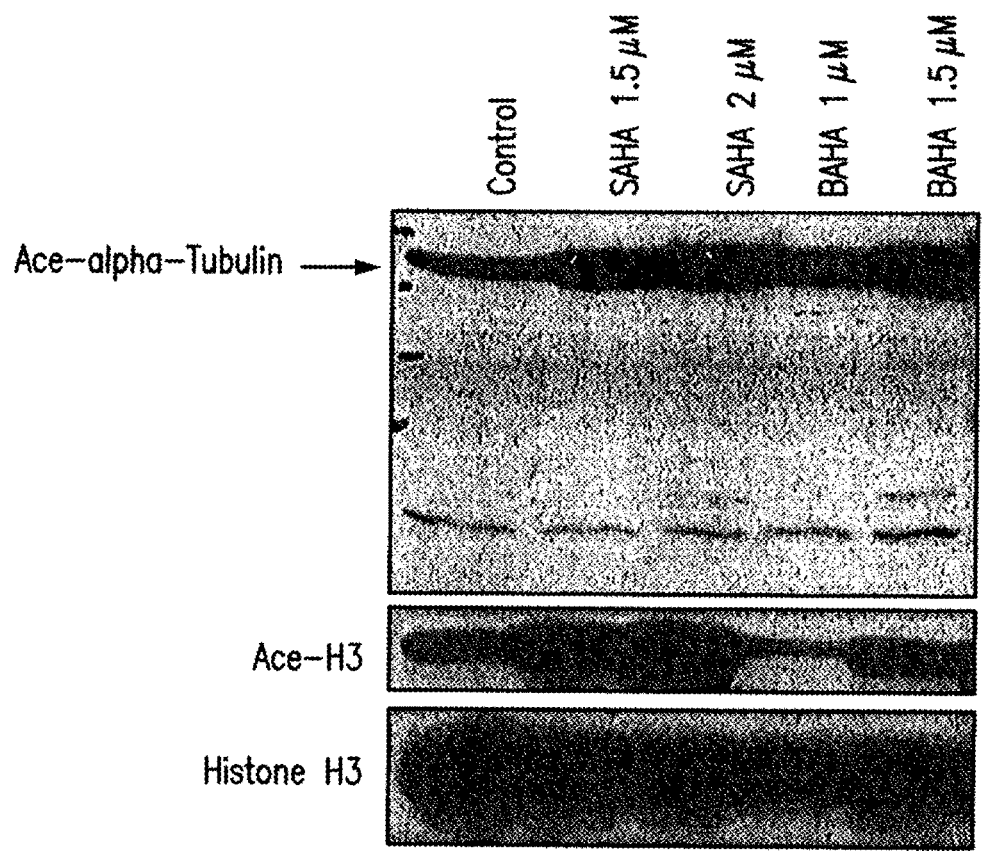
FIG. 2 Characterization of BAHA as an inhibitor of HDAC 6. BAHA induced accumulation of acetylate tubulin (Ace-alpha-tubulin) but not acetylated histone H3 (Ace-H3) at 1.0 μM and 1.5 μM BAHA. Control, (DMSO) did not induce accumulation of acetylated tubulin or acetylated histones. SAHA, an inhibitor of HDAC 1, 2, 3, and 6, induced accumulation of acetylated tubulin and acetylated histones H3. Histone H3 is loading control.

It was shown (Haggerty et al. *PNAS* 100:4389-4394, 20003) that in A549 cells, a human non-small cell lung cancer cell line, culture with 0.2, 2 or 20 μM tubacin caused an accumulation of acetylated tubulin but not acetylated histone H3 (FIG. 1). Nil-tubacin (Table 2), a derivative of tubacin that does inhibit HDAC 6, did not induce the accumulation of acetylated α-tubulin in the A549 cells. Trichostatin A (TSA), a pan-HDACi, which inhibits class I HDACs and class IIb HDACs caused the accumulation of acetylated α-tubulin and acetylated histone H3 (FIG. 1). BAHA is a selective inhibitor of HDAC 6 (Kozikowski *J Med Chem* 51:4370-4373, 2008) at 1 and 1.5 μM. LNCaP, a human prostate cancer cell line cultured with 1.0 or 1.5 μM BAHA caused the accumulation of acetylated α-tubulin, with little or no accumulation of acetylated histone H3 (FIG. 2). Suberyl hydroxamic Acid (SAHA) (vorinostat), a pan HDAC inhibitor similar in its activity to TSA, at 1.5 and 2.0 μM caused an increase in accumulation of acetylated α-tubulin and acetylated histone H3. Thus, the HDAC 6-selective inhibitors, tubacin and BAHA, caused an accumulation of acetylated α-tubulin, but not acetylated histones, while TSA and SAHA, inhibitors of class I HDACs, HDAC 1, 2, 3, and 8, and class IIb HDACs, HDAC 6 and 10, cause the accumulation of acetylated α-tubulin and acetylated histones.

Selective Inhibitor of HDAC 6 Increase Sensitivity of Human Transformed Cells to Cell Death Induced by Anti-Cancer Agents A. Selective Inhibitor of HDAC 6 Increases Sensitivity of LNCaP Cells to SAHA-Induced Cell Death.

Figure 3:
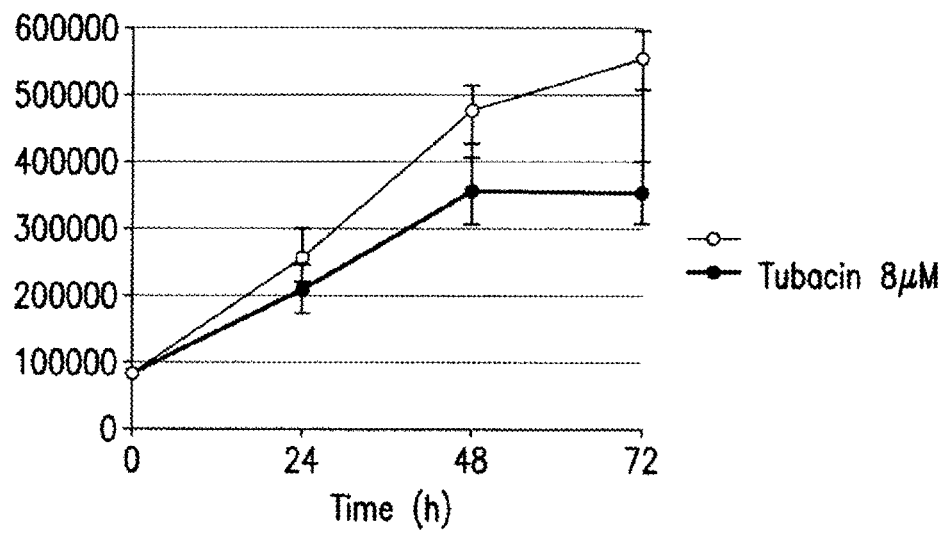
FIG. 3 LNCaP cells (human prostate Cancer) cultured with tubacin do not induce cell death. Left panel: cell growth. DMSO control (red line), tubacin 8 μM (blue line). Right panel: cell viability.
Figure 3:
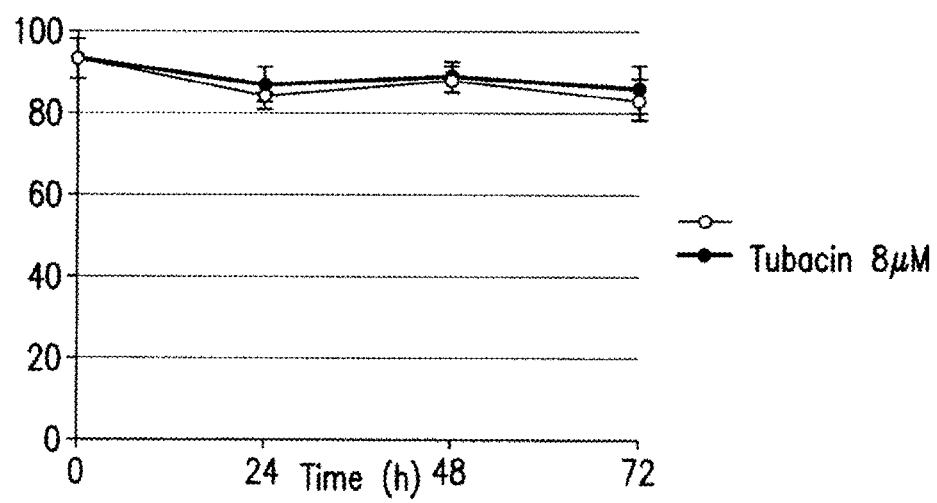
Figure 4:
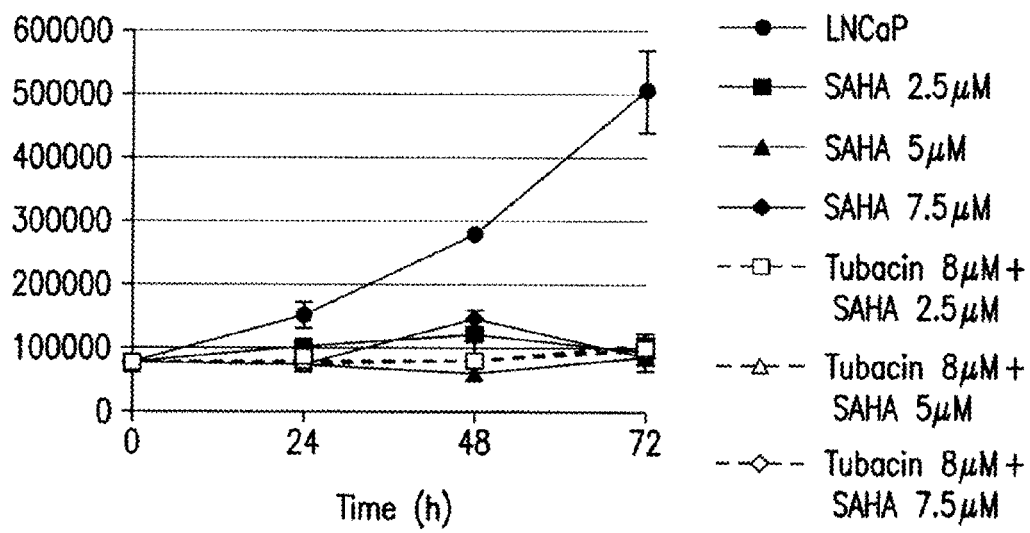
FIG. 4 LNCaP cells cultured with tubacin in combination with SAHA (dashed lines), or SAHA alone (solid lines). Cell growth (left panel) and cell viability (right panel) were determined at 24, 48 and 72 hrs after onset of culture. In each culture, the combination of tubacin plus SAHA caused a significantly (horizontal bar is 2 S.D.) greater loss in viability than culture with SAHA alone.
Figure 4:
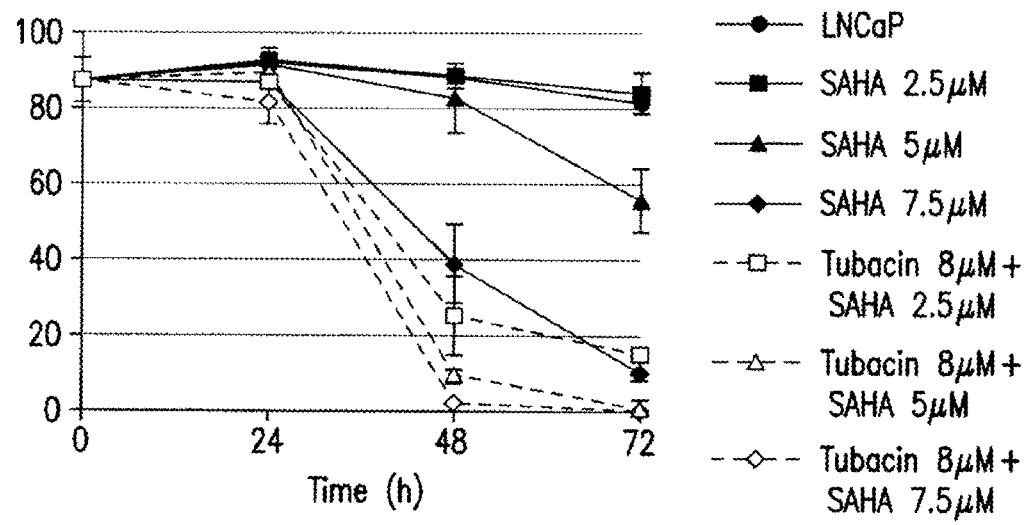

The selective inhibitor of HDAC 6, tubacin, cultured with LNCaP did not cause cell death up to 72 hrs in culture (FIG. 3). Tubacin, significantly enhanced SAHA-induced cell death in LNCaP cells (FIG. 4). The rate of cell growth was markedly decreased in cultures with 2.5 μM or 5 μM or 7.5 μM SAHA or SAHA plus 8 μM tubacin (FIG. 4). 2.5 μM or 5 μM or 7.5 μM SAHA caused no detectable, 45% LNCaP cell death and 90% cell death at 72 hrs in culture, respectively. Simultaneous addition of 8 μM tubacin and 2.5 or 5 μM SAHA resulted in a significant increase in cell death compared to cells cultured with SAHA alone, namely, 85% and 100%, respectively (FIG. 4). LNCaP cultured with 7.5 μM SAHA (not attainable in clinical trials. Kelly et al. *J Clin Oncology* 23:3923-3931, 2005) caused 40% cell death compared to 100% cell death in cultures with 8 μM tubacin plus 7.5 μM SAHA after 8 hrs.

Figure 5:
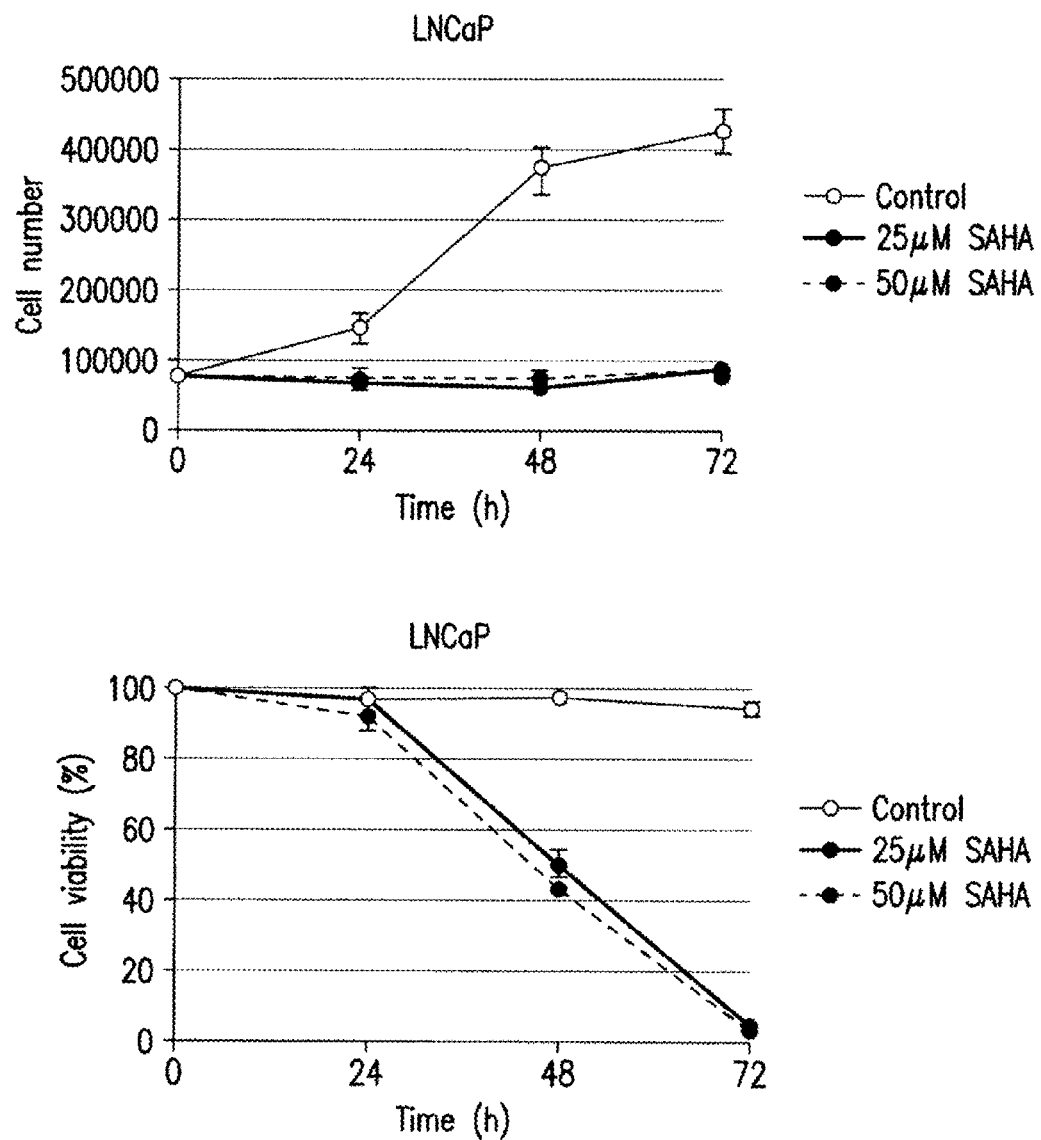
FIG. 5 LNCaP cells cultured with 25 μM (blue line) or 50 μM (green line) SAHA for 72 hrs caused growth inhibition (left panel) and 100% cell death (right panel).

The extent of cell death observed in LNCaP cultured with 5 μM SAHA plus 8 μM tubacin is similar to the level of cell death observed with 25 or 50 μM SAHA alone by 72 hrs of culture (FIG. 5). The clinically attainable concentration of SAHA in therapeutic trials is 2.0 to 4.0 μM at doses that are tolerated by patients.

Figure 6:
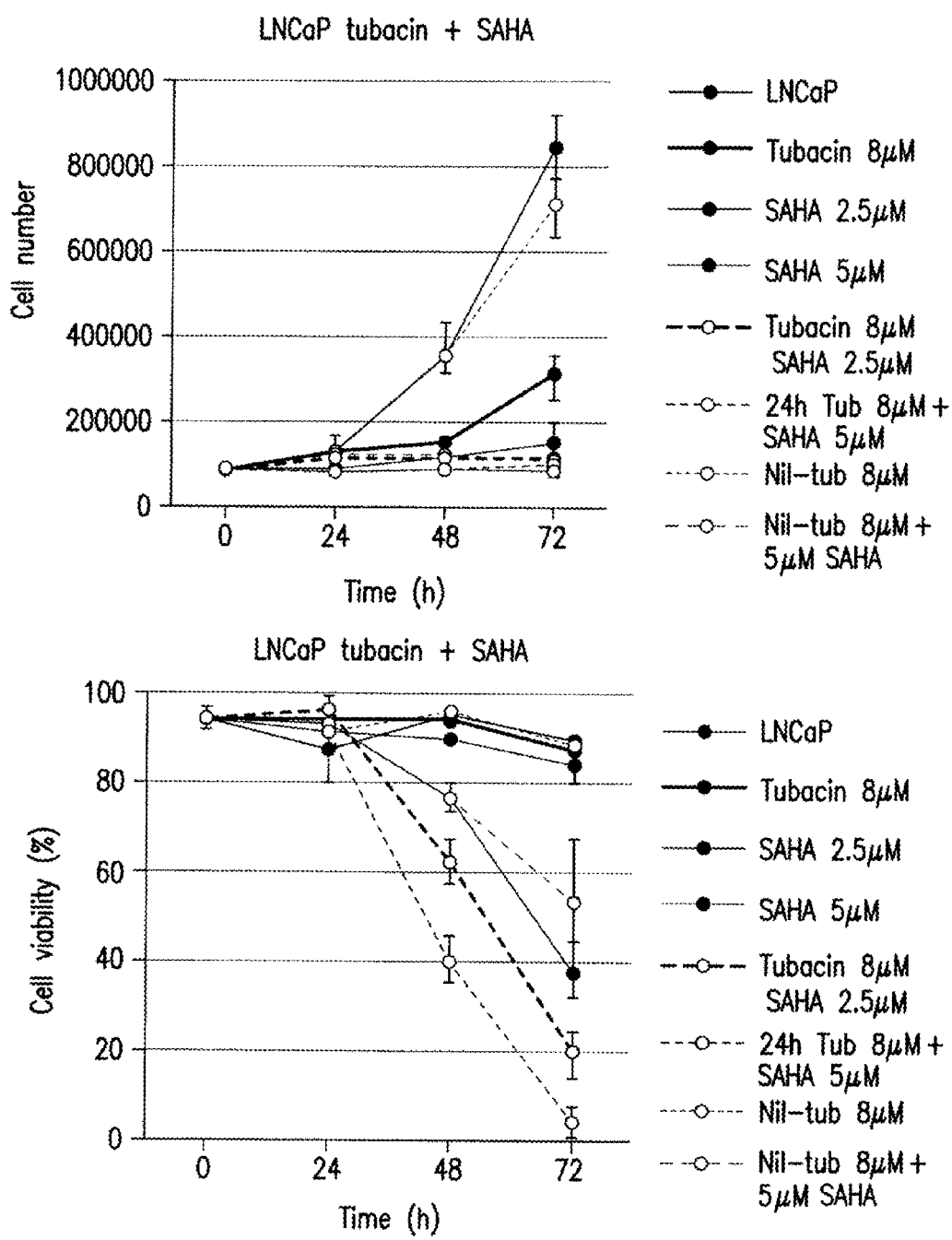
FIG. 6 LNCaP cultured with nil-tubacin, tubacin, or SAHA alone (solid lines) and in combination of nil-tubacin plus SAHA or tubacin plus SAHA (broken lines). Nil-tubacin (pink), unlike tubacin (blue), did not increase SAHA induced cell death.

To determine whether tubacin enhancement of SAHA-induced cell death was due to an off-target HDAC 6 effect, LNCaP cells were cultured with 8 μM nil-tubacin alone or with 8 μM nil-tubacin plus 5 μM SAHA. Nil-tubacin alone did not have a detectable effect on cell growth or cell viability and the combination of nil-tubacin plus SAHA did not result in enhanced cell death compared to cultures with SAHA alone (FIG. 6).

B. Selective Inhibition of HDAC 6 Increases Sensitivity of LNCaP cells to Doxorubicin-Induced Cell Death.

Figure 7:
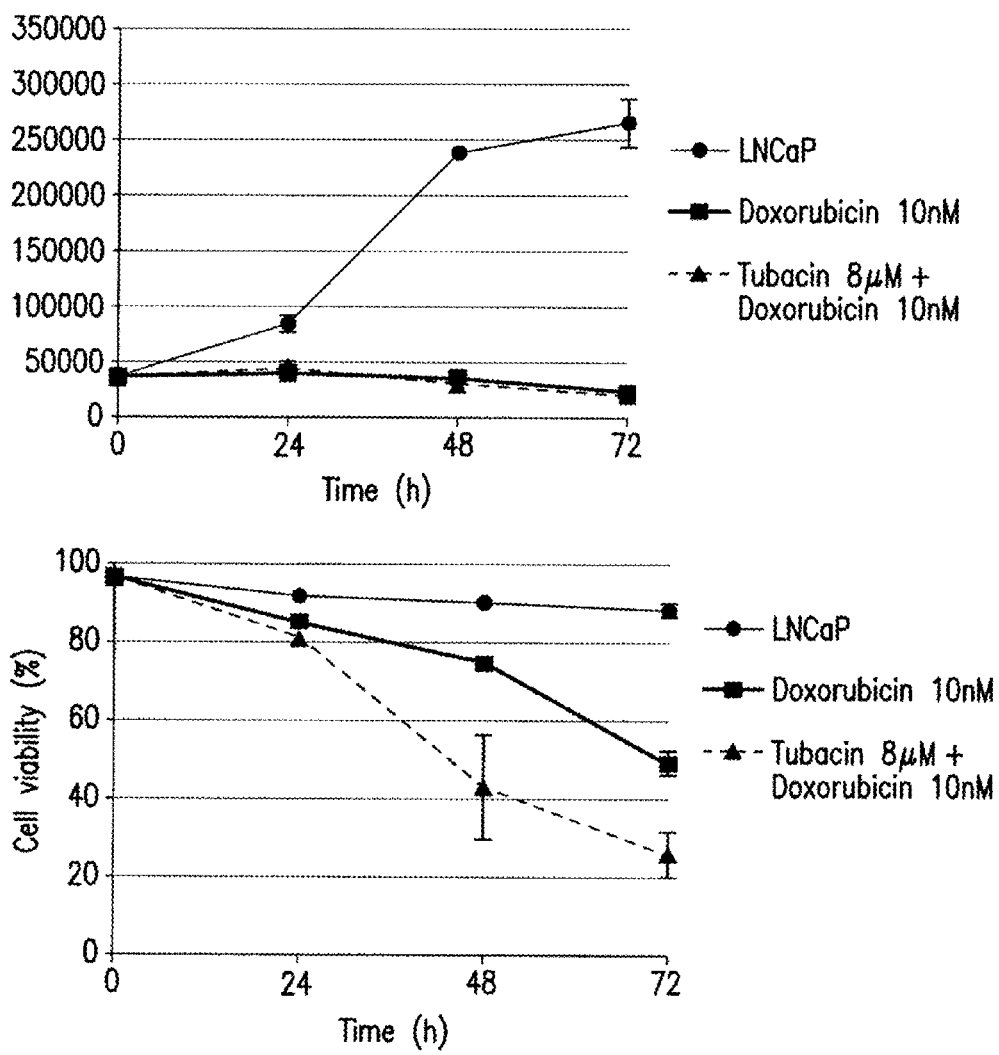
FIG. 7 LNCaP cells cultured with 8 μM tubacin plus 10 nM doxorubicin (green line) has significantly greater death than 10 nM doxorubicin alone (blue line). Control (DMSO) (red line). Left panel: cell growth. Right panel: cell viability.
Figure 8:
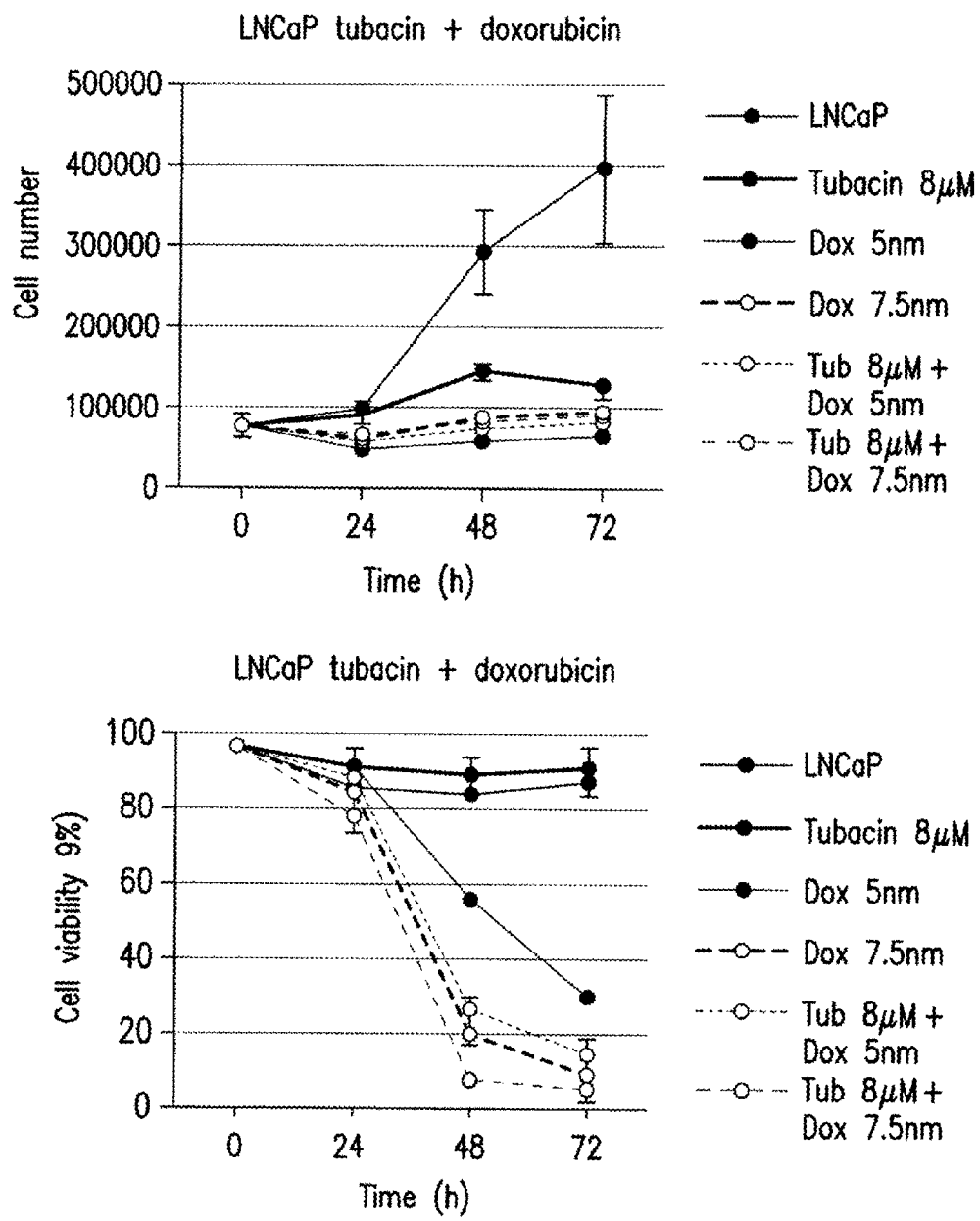
FIG. 8 LNCaP cells cultured with 8 μM tubacin (blue), 5 nM doxorubicin (dark blue) or 7.5 nM doxorubicin (green) and LNCaP cells cultured with doxorubicin plus tubacin (dashed lines). Left panel: cell growth. Right panel: cell viability.

Selective inhibition of HDAC 6 with tubacin significantly enhanced doxorubicin-induced cell death of LNCaP cells (FIG. 7). The rate of cell growth was decreased in cultures with 10 nM doxorubicin alone and, markedly more decreased in cultures with 10 nM doxorubicin plus 8 μM tubacin, 50% and 75% loss in viability, respectively (FIG. 7). 5 nM doxorubicin and 7.5 nM doxorubicin caused 40% and 80% cell death after 48 hrs in culture, respectively, compared to cultures with 8 μM tubacin plus 5 nM doxorubicin or plus 7.5 nM doxorubicin which caused 75% and 95% cell death by 48 hrs culture, respectively (FIG. 8).

C. Selective Inhibition of HDAC 6 Increases Sensitivity of LNCaP Cells to Etoposide-Induced Cell Death.

Figure 9:
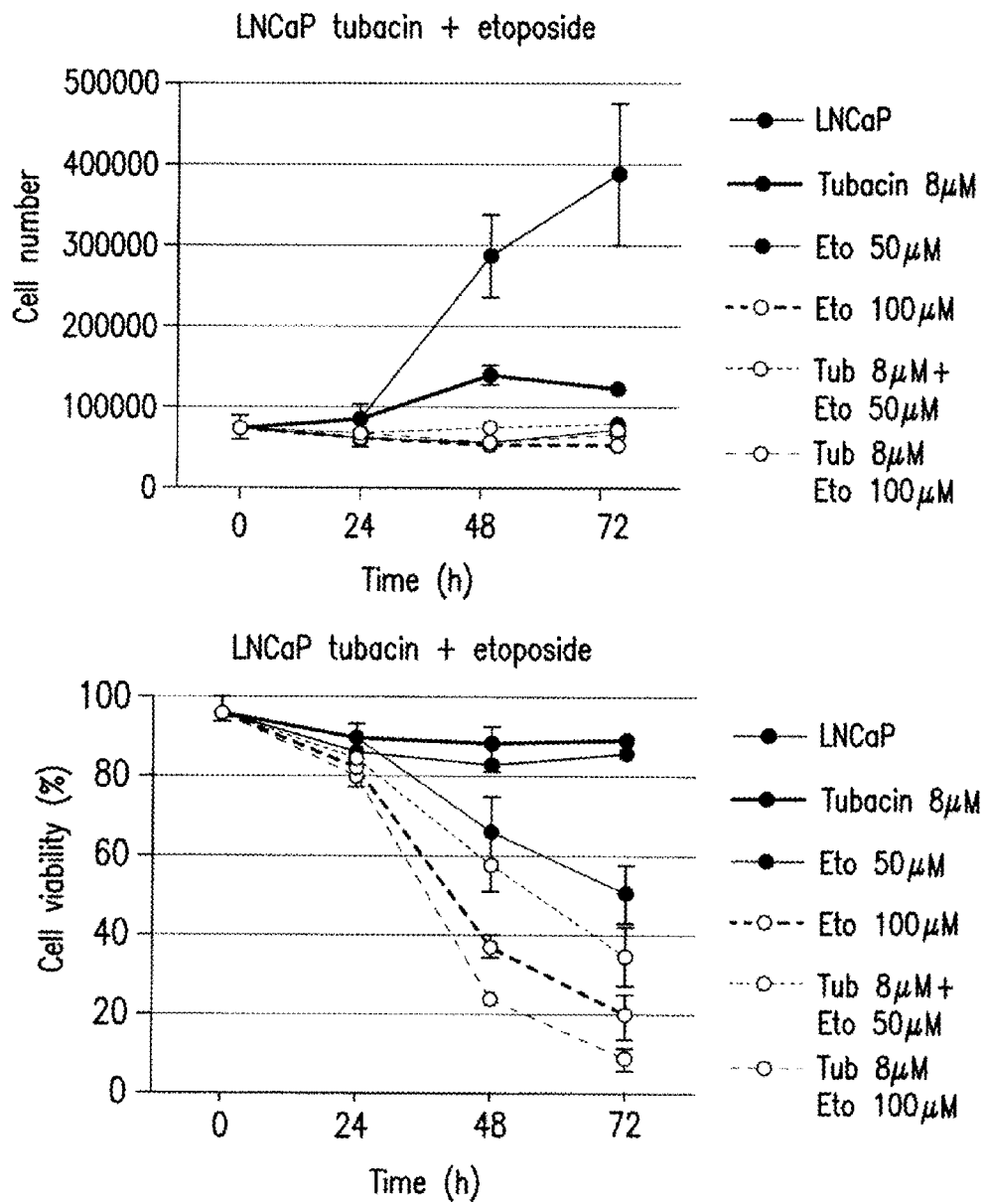
FIG. 9 LNCaP cells cultured with 8 μM tubacin plus 50 μM etoposide (blue); 8 μM tubacin plus 100 μM etoposide (green) (dashed lines) and LNCaP cultured alone with 8 μM tubacin (blue); 50 μM etoposide (dark blue) or 100 μM etoposide (green) (unbroken lines). Left panel: cell growth. Right panel: cell viability.

Selective inhibition of HDAC 6 with tubacin significantly enhanced etoposide-induced cell death of LNCaP cells (FIG. 9). The rate of cell growth of LNCaP was decreased by 8 μM tubacin alone and markedly decreased in cultures with 50 or 100 μM etoposide alone and tubacin plus etoposide in 72 hrs of culture (FIG. 9). 8 μM tubacin did not induce LNCaP cell death, 50 μM and 100 μM etoposide caused 50% and 80% cell death after 72 hrs in culture, respectively, compared to cultures with 8 μM tubacin plus 50 μM etoposide which caused 65% and 95% cell death at 72 hrs in culture, respectively (FIG. 9).

D. Selective Inhibition of HDAC 6 Increases Sensitively of MCF-7 Cells to SAHA, Doxorubicin and Etoposide-Induced Cell Death.

Figure 10:
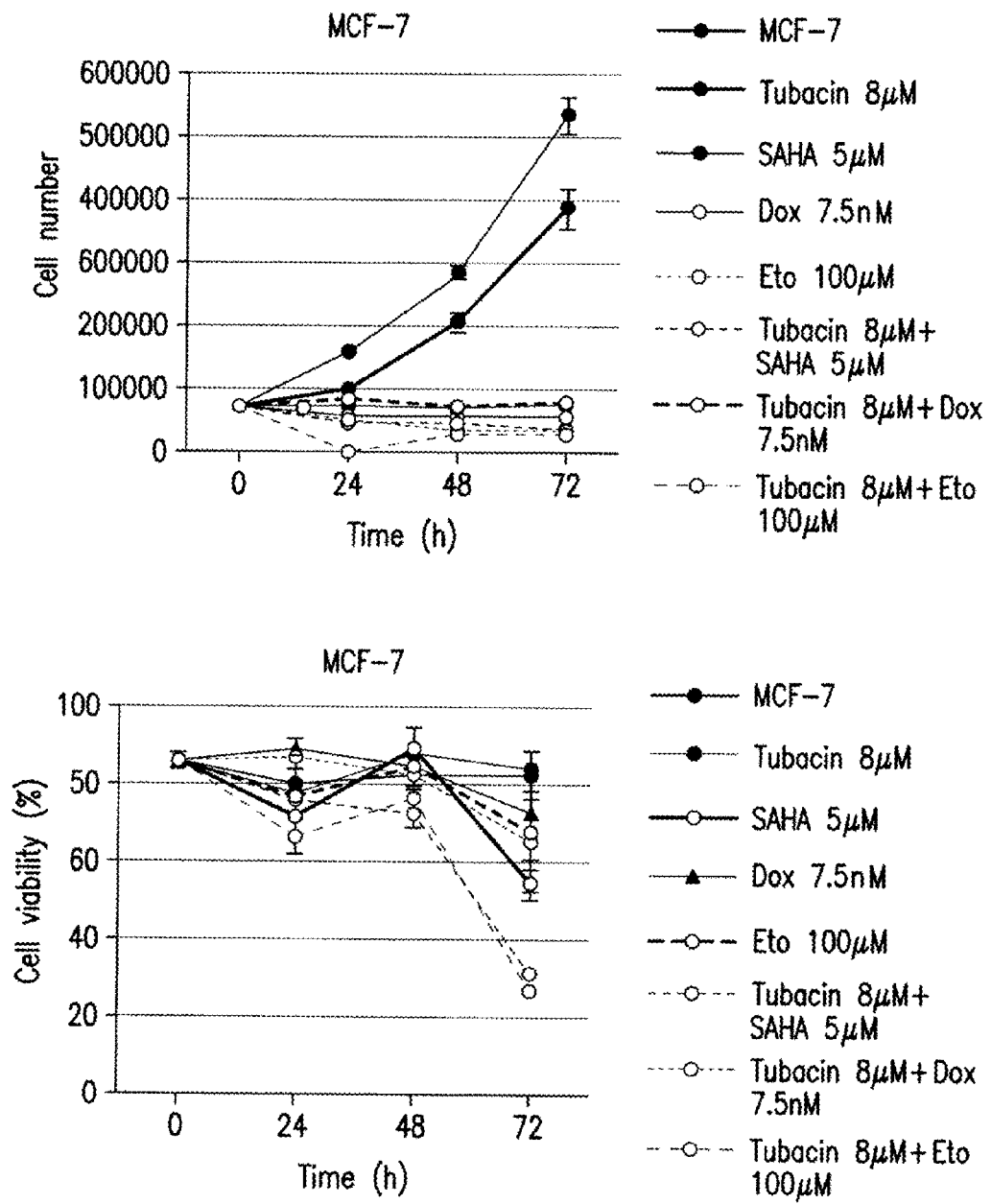
FIG. 10 MCF-7 cells cultured without (red) or with 8 μM tubacin (light blue), 5 μM SAHA (dark blue), 7.5 nM doxorubicin (green) or 100 μM etoposide (pink) (unbroken lines) and each of these drugs cultured plus tubacin (dashed lines). Left panel: cell growth. Right panel: cell viability.

Selective inhibition of HDAC 6 with tubacin significantly enhanced SAHA, doxorubicin and etoposide-induced cell death of MCF-7 cells (FIG. 10). The rate of cell growth was somewhat decreased by 8 μM tubacin, and markedly decreased by 5 μM SAHA, 7.5 nM doxorubicin or 100 μM etoposide, and by 8 μM tubacin plus 5 μM SAHA, or 7.5 nM doxorubicin or 100 μM etoposide in 72 hrs (FIG. 10) 8 μM tubacin did not induce MCF-7 cell death, 5 μM SAHA, 7.5 nM Doxorubicin or 100 μM etoposide caused 40%, 25% and 30% cell death, respectively, compared to cultures with 8 μM tubacin plus 5 μM SAHA, or plus 7.5 nM doxorubicin or plus 100 μM etoposide which caused 65%, 45%, and 70% cell death at 72 hrs, respectively (FIG. 10).

E. Selective Inhibition of HDAC 6 with BAHA Sensitizes LNCaP Cells to SAHA-Induced Cell Death.

Figure 11A:
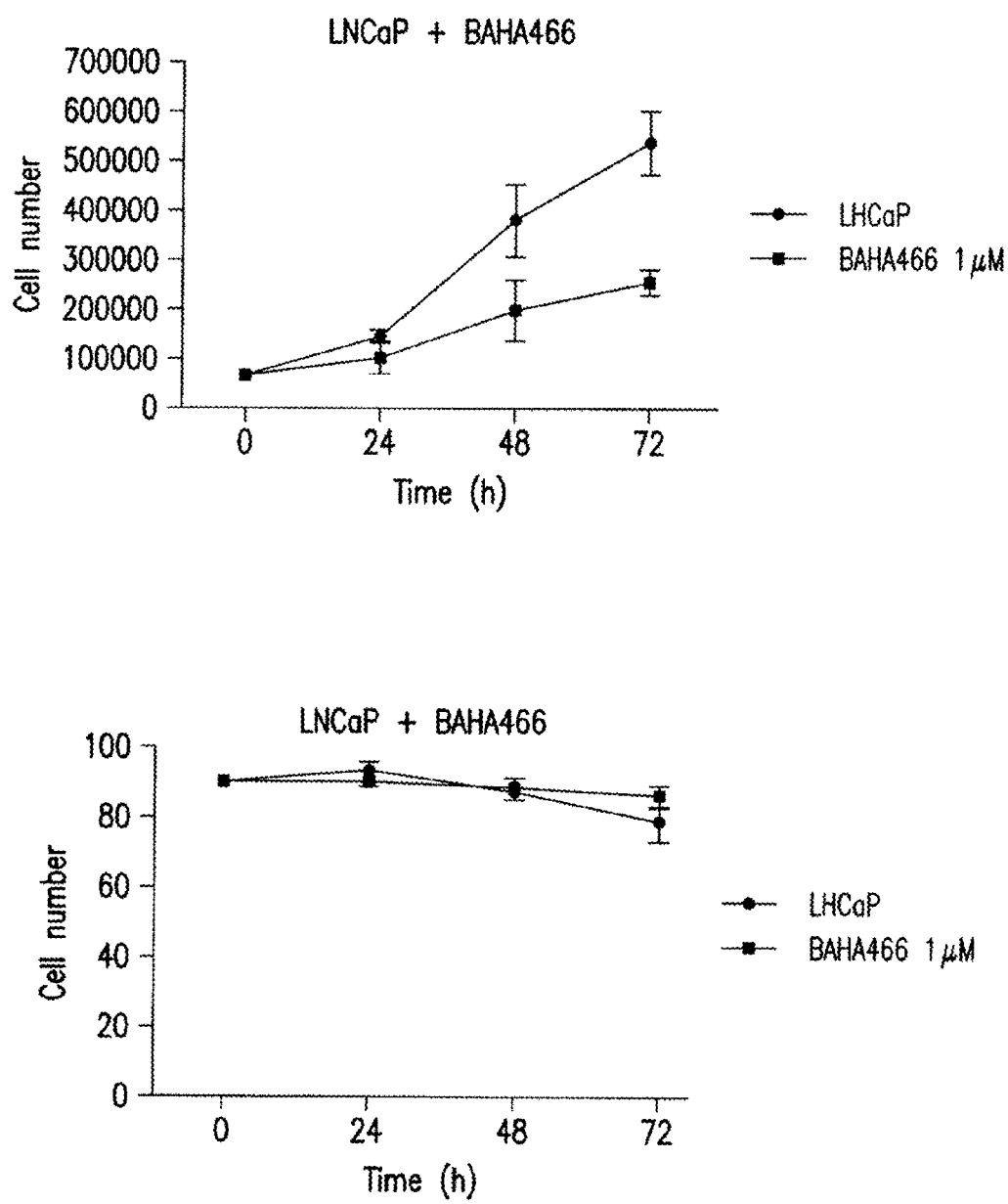
FIG. 11 LNCaP cells cultured with 1 μM BAHA; 1.25 μM SAHA. 2.5 μM SAHA or 5 μM SAHA (solid lines) and LNCaP cells cultured with 1 μM SAHA plus 1.5 μM or 2.5 μM SAHA or 5 μM SAHA (dashed lines). Left panel: cell growth. Right panel: cell viability.
Figure 11B:
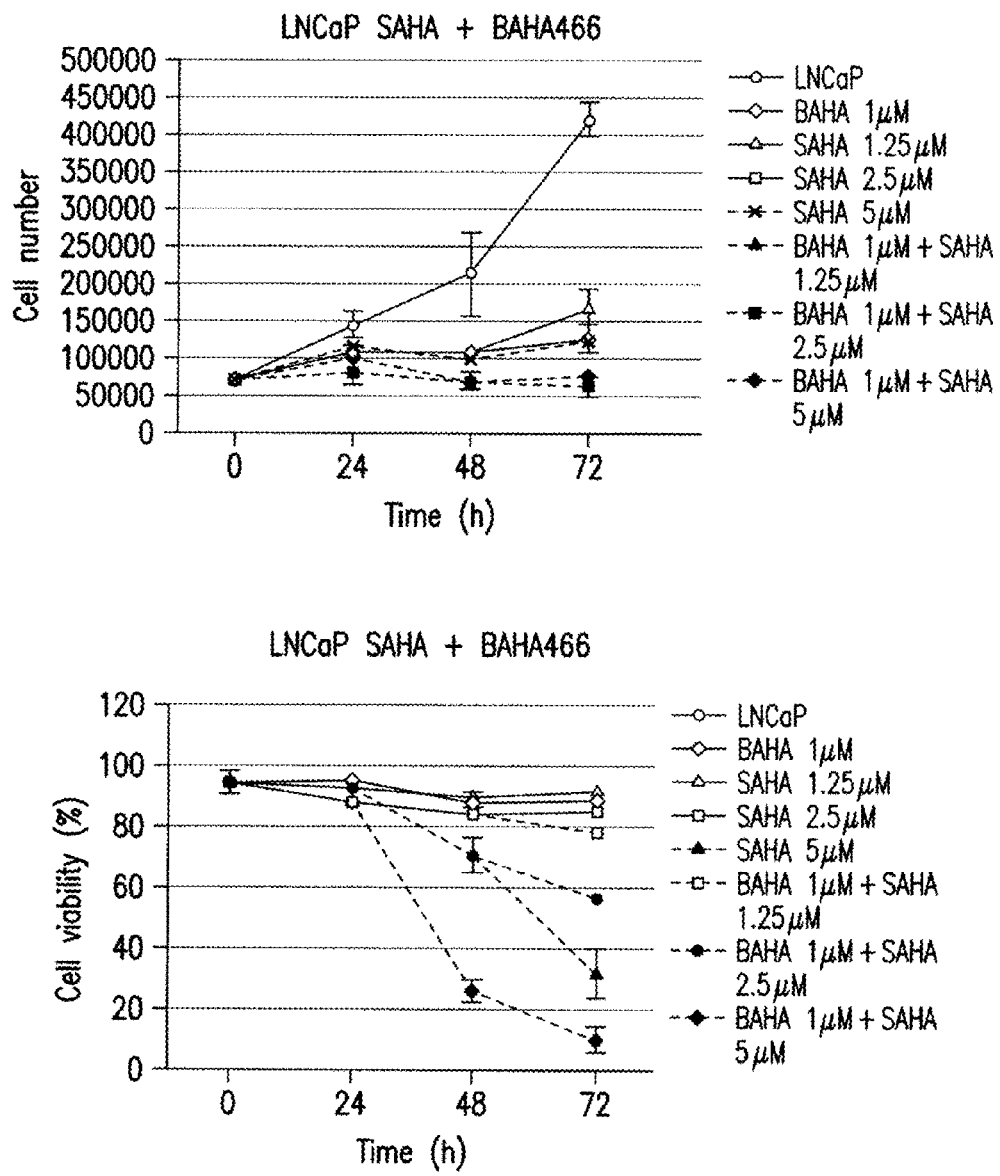

Further support of the discovery that selective inhibition of HDAC 6 markedly sensitizes transformed cells to anti-cancer drugs was obtained with the selective HDAC 6 inhibitor, BAHA. 1 μM BAHA in culture with LNCaP cells caused moderate inhibition of cell growth but no cell death (FIG. 11A). SAHA in culture with LNCaP cells caused no detectable cell death at 1.25 μM, less than 10% cell death at 2.5 μM and 65% cell death at 5 μM after 72 hrs of culture (FIG. 11B). In cultures of LNCaP cells with 1 μM BAHA plus 1.25, 2.5 or 5 μM SAHA, cell death at 72 hrs in culture was 20%, 40%, and 90%, respectively (FIG. 11B).

Figure 12:
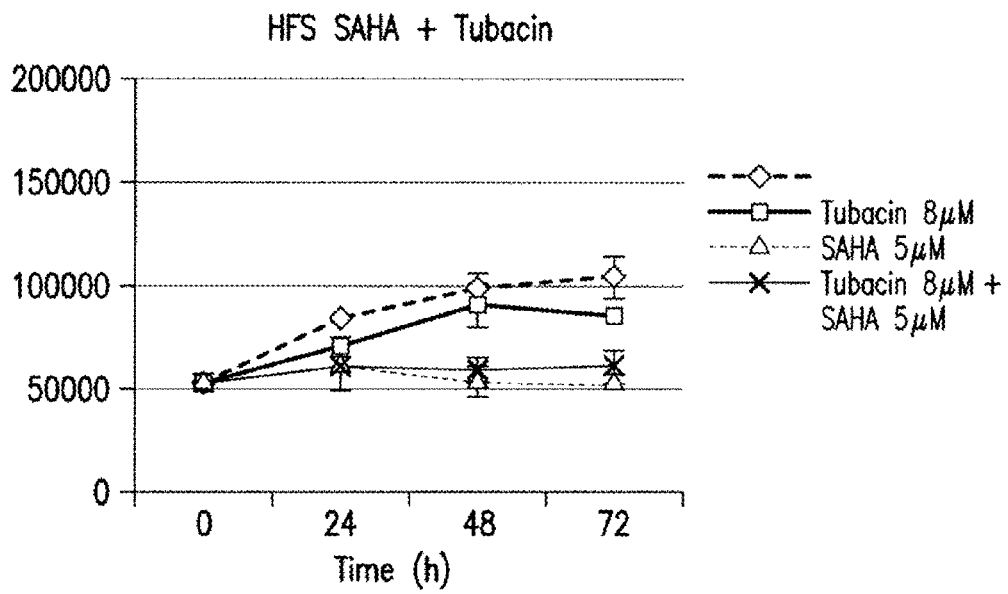
FIG. 12 Normal human foreskin cells (HFS) cells cultured without (blue) or with 8 μM tubacin (red) or 5 μM SAHA (yellow) or 8 μM tubacin plus 5 μM SAHA (green). Left panel: cell growth. Right panel: cell viability.
Figure 12:
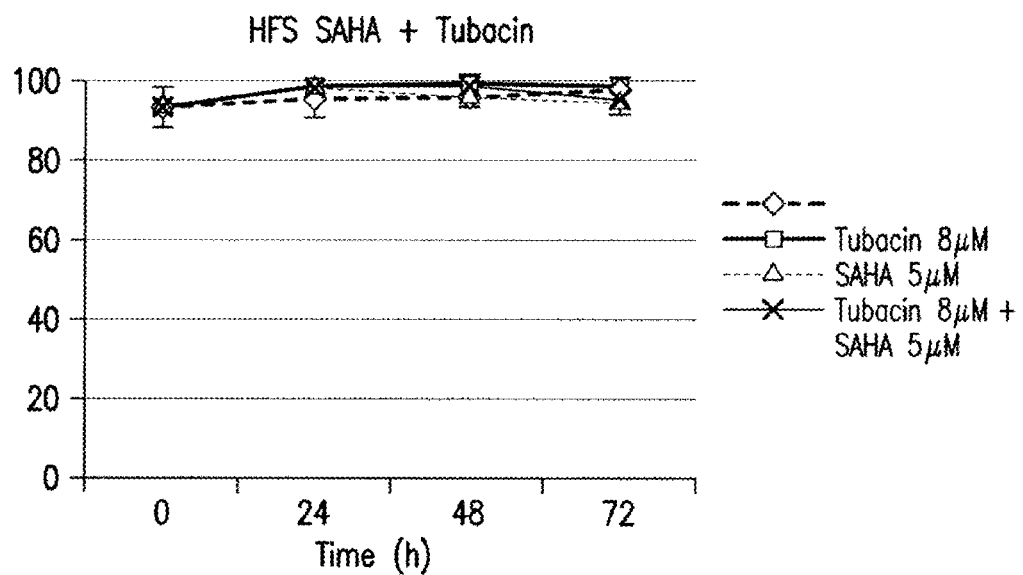
Figure 13:
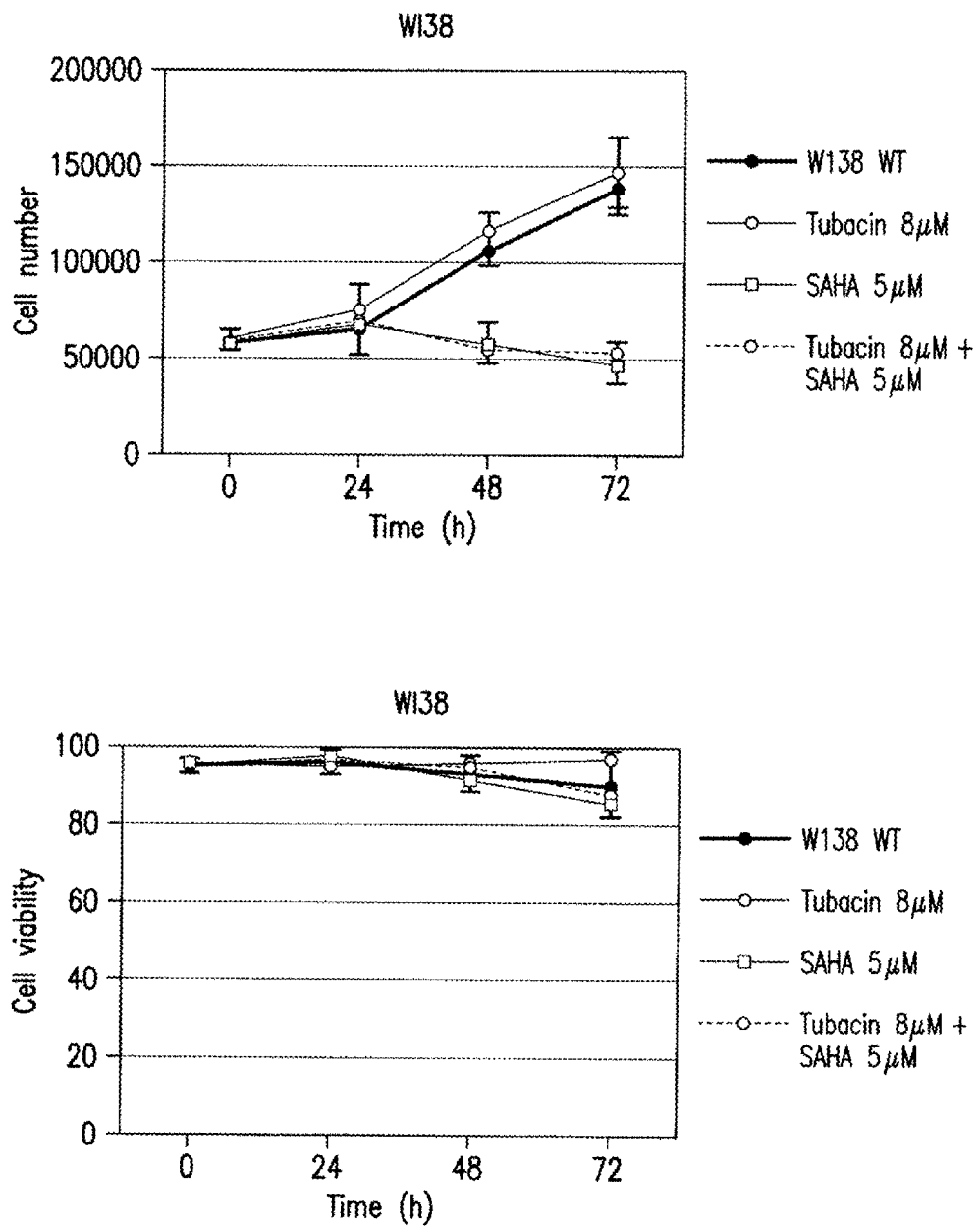
FIG. 13 Human embryonic fibroblast (WI38) cells cultured without (red) or with 8 μM, tubacin (light blue) or 5 μM SAHA (dark blue) or 8 μM tubacin plus 5 μM SAHA (dark line). Left panel: cell growth. Right panel: cell viability.

Selective Inhibition of HDAC 6 with Tubacin does not Make Normal Cells Sensitive to SAHA-Induced Cell Death Culture of HFS cells with 8 μM tubacin plus 5 μM SAHA or with either drug alone did not cause cell death (FIG. 12). These studies were performed with normal human foreskin cells (HFS) (FIG. 12). Culture of WI38 cells with 8 μM tubacin plus 5 μM SAHA or either drug alone did not cause cell death. WI38 is a normal human embryonic fibroblast cell (FIG. 13).

LNCaP Cells in which HDAC 6 Expression is Genetically Suppressed

Figure 14A:
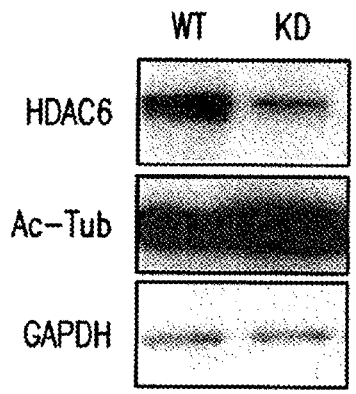
FIG. 14 Downregulation of HDAC 6 expression by treating LNCaP cells with shRNA for HDAC 6: (A)—Western Gel Blot for HDAC 6, acetylated tubulin (Ac-Tub) and GAPDH (glyceraldehyde phosphate dehydrogenase as loading control). (B) LNCaP with downregulated HDAC 6 had no loss of viability (lower panel) and modest inhibition of cell growth (upper panel).
Figure 14B:
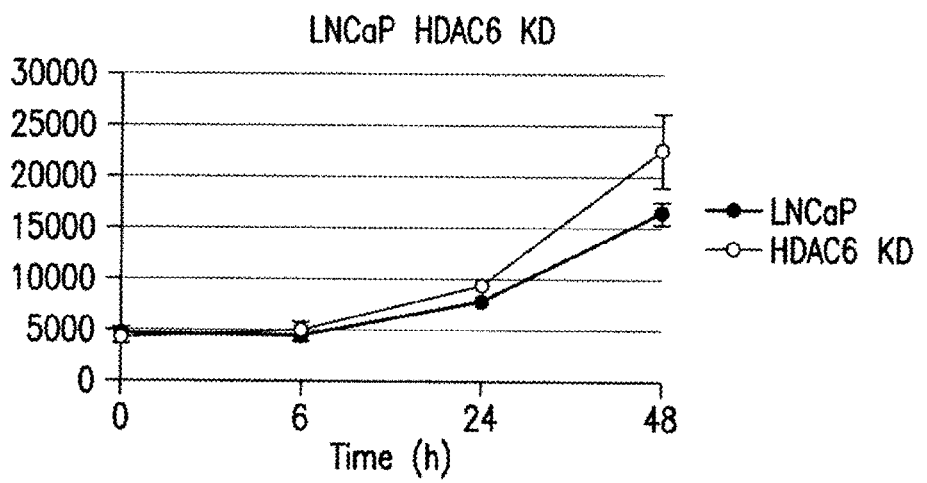
Figure 14B:
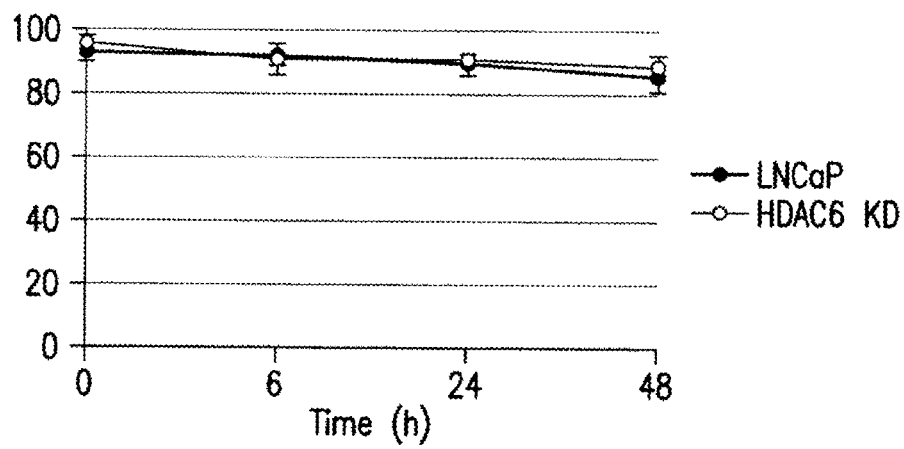
Figure 15:
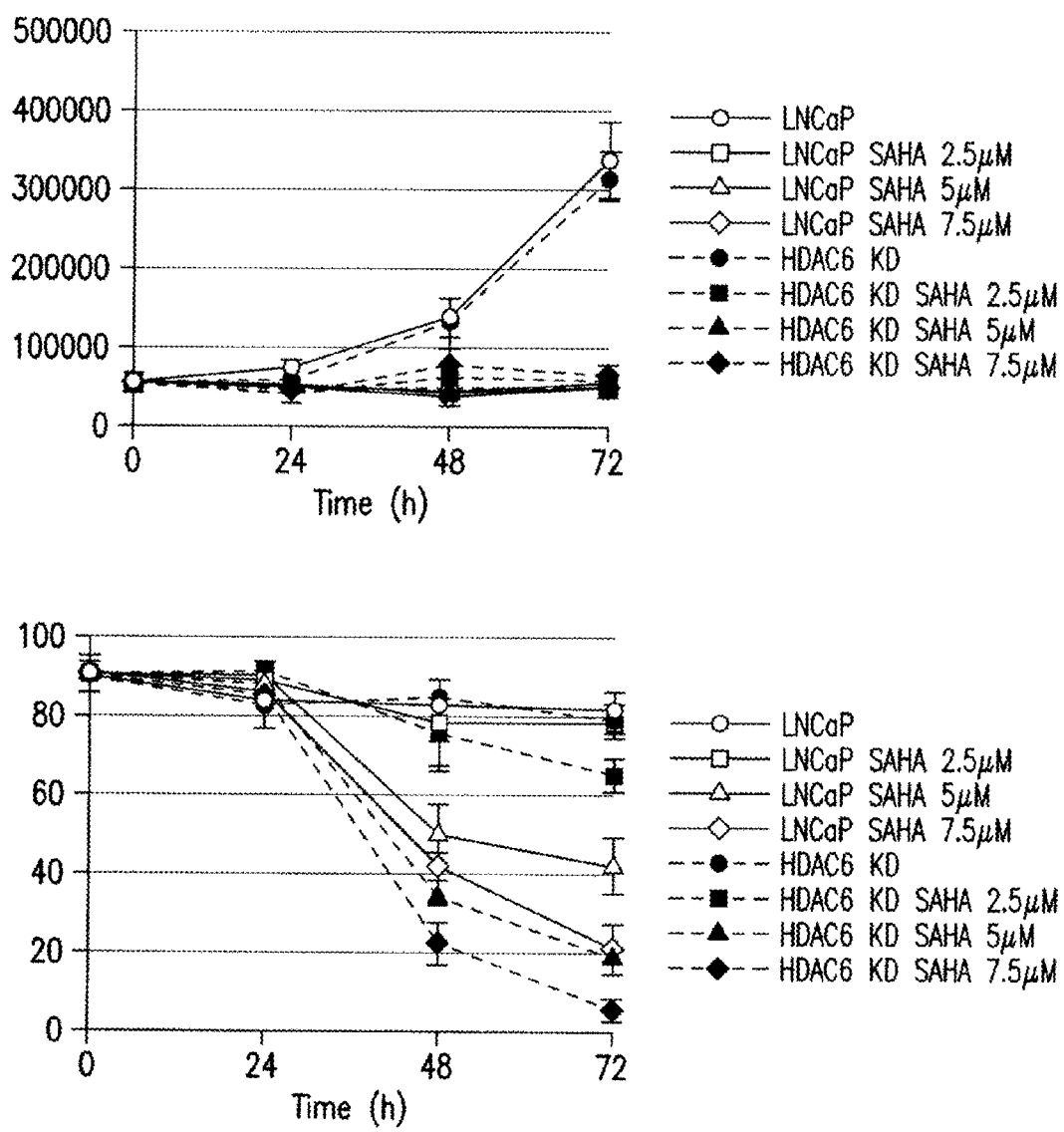
FIG. 15 LNCaP cells with downregulation of HDAC 6 (KD) cultured with 2.5 SAHA (dark blue) 5 μM SAHA (green) or 7.5 μM (black) SAHA (dashed lines) and wild type LNCaP cultured with 2.5 μM SAHA (dark blue), 5 μM SAHA (green) or 7.5 μM SAHA (black) (solid lines).

LNCaP cells in which HDAC 6 expression was suppressed (FIG. 14A) showed no decrease in viability compared to wild type LNCaP (FIG. 14B). LNCaP HDAC 6 knockdown cells cultured with 2.5, 5.0, or 7.5 μM SAHA had 25%, 80%, and 95% cell death compared to wild type LNCaP, no cell death, 35% and 75% respectively at 72 hrs (FIG. 15).

Figure 16:
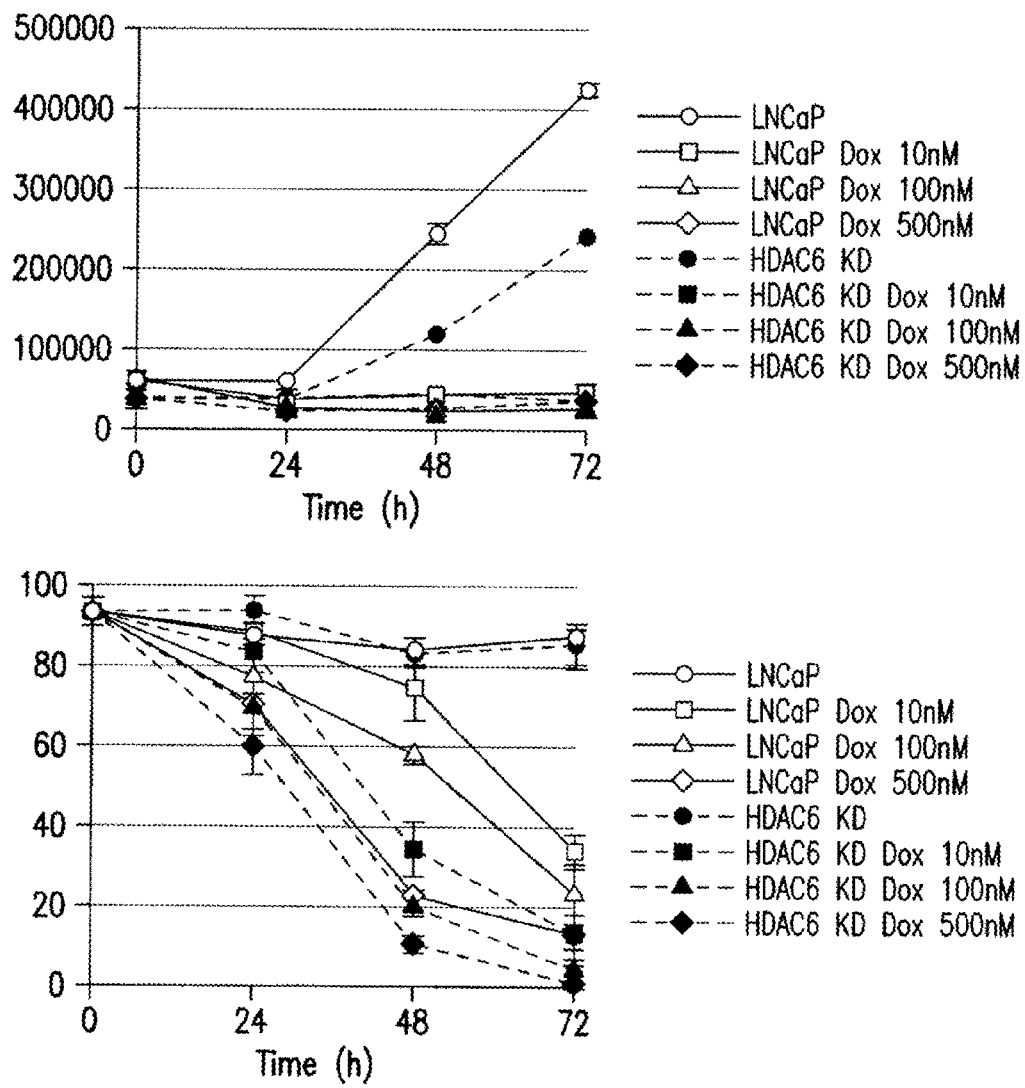
FIG. 16 LNCaP cells with downregulated HDAC 6 (KD) cultured without (red) or with 10 nM doxorubicin (dark blue), 100 nM doxorubicin (green) or 500 nM (black) (dashed lines) and wild type LNCaP cells cultured without (red) or with 10 nM doxorubicin, (blue), 100 nM doxorubicin (black) (solid lines).

LNCaP HDAC 6 knock down cells cultured with 10 nM, 100 nM and 500 nM doxorubicin had 85%, 90%, and 95% cell death compared to wild type LNCaP, 45%, 75%, and 85% cell death, respectively at 72 hrs (FIG. 16).

Figure 17:
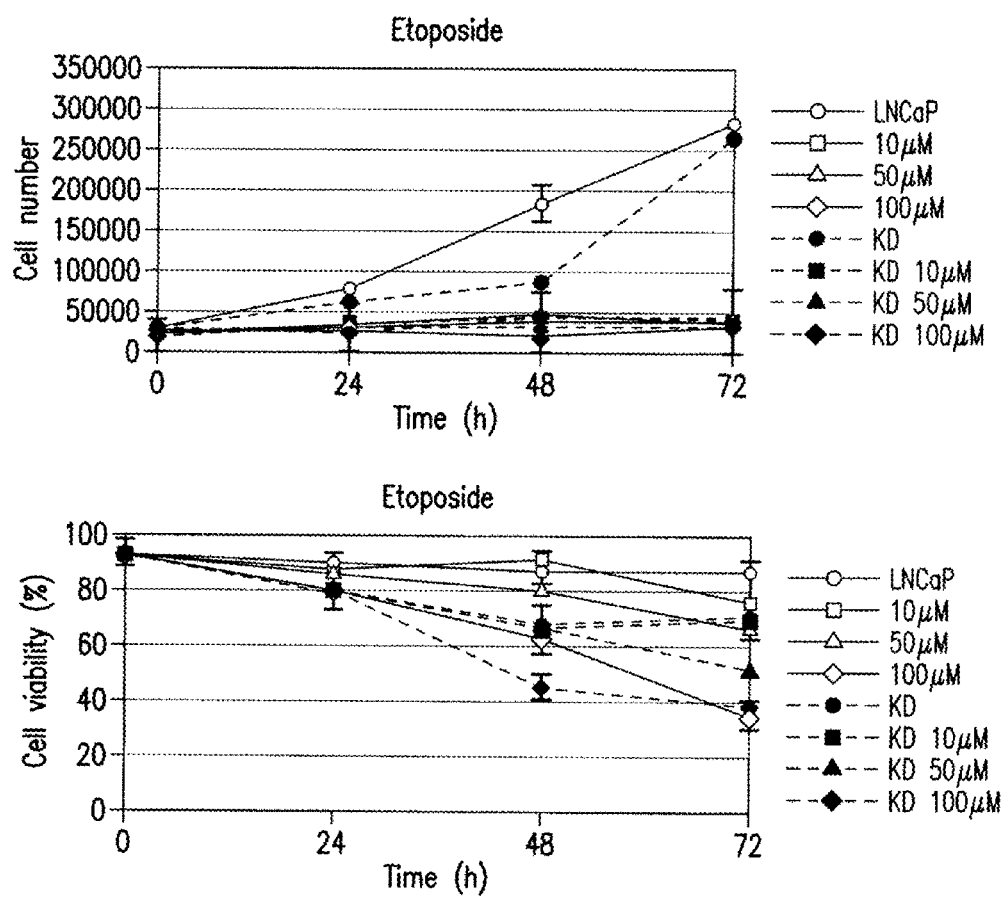
FIG. 17 LNCaP cells with downregulated HDAC 6 (KD) cultured without (●) or with 10 mM etoposide (•), 50 mM etoposide (Δ), or 100 mM etoposide (◇) (dashed lines) and wild type LNCaP culture without (●), or with 10 mM etoposide (•), 50 mM etoposide (Δ) or 100 μM etoposide (◇) (solid lines).

LNCaP HDAC 6 knockdown cells cultured with 10 μM, 50 μM or 100 μM etoposide had 20%, 35%, and 55% cell death compared to wild type LNCaP which had 10%, 30%, and 40% cell death at 48 hrs in culture (FIG. 17).

III. Significance and Conclusion

It has now been discovered that selective inhibition of HDAC 6 markedly increases the sensitivity to transformed cells but not normal cells to anti-cancer agents. This discovery has considerable therapeutic significance. One of the major challenges in the treatment of cancer patients with chemotherapy or with HDAC inhibitors such as SAHA (vorinostat) is the fact that only a portion of patients with cancers respond to these therapies. Further, development of resistance of cancers to these therapies is a common occurrence. Increasing the sensitivity of cancer cells to anti-cancer therapy has the potential to significantly increase the therapeutic efficacy of these agents across a spectrum of different types of cancers. The basis of cancer cell resistance to anti-cancer agents is not well understood. The selective inhibition of HDAC 6 causes the accumulation of acetylated proteins that play an important role in cell survival, cell proliferation, and cell migration. It can be speculated that the efficacy of selective inhibition of HDAC 6 and increasing the sensitivity of cancer cells to various anti-cancer agents is owing to the fact that selective inhibition of HDAC 6, while not inducing normal or transformed cell death itself, alters the protein structure and function of proteins that effect various cell pathways that are dysregulated in cancer cells (Jones et al. *Science* 321:1801-1806, 2008). These studies indicate the importance of the development of selective inhibitors of HDAC 6 that will be well tolerated in the therapy of patients. See Kozikowski et al. *J Med Chem* 51:4370-4373, 2008, reviewed in Marks, P. A. and Xu, W.-S. Histone deacetylase inhibitors: Potential in cancer therapy. *J Cellular Biochemistry*, E-Pubmed, 2009).

IV. Synopsis

The present discovery demonstrates that two HDAC 6-selective inhibitors, tubacin and BAHA, significantly increase the sensitivity of transformed cells, LNCaP (a human prostate cell), and MCF-7 (a human breast adenocarcinoma cell) to cell death induced by the anti-cancer drugs SAHA, doxorubicin and etoposide, while normal cells are not induced to cell death by these drugs.

TABLE 1

Zinc-Dependent Histone Deacetylases**

| HDAC | Localization | Size (AA) | Chromosomal site | Tissue distribution* |
|---|---|---|---|---|
| Class I | | | | |
| HDAC1 | Nucleus | 483 | 1p34.1 | ubiquitous |
| HDAC2 | Nucleus | 488 | 6p21 | ubiquitous |
| HDAC3 | Nucleus | 423 | 5q31 | ubiquitous |
| HDAC8 | Nucleus | 377 | Xq13 | ubiquitous |
| CLASS IIa | | | | |
| HDAC4 | Nuc/Cyt | 1084 | 2q372 | H, SM, B |
| HDAC5 | Nuc/Cyt | 1122 | 17q21 | H, SM, B |
| HDAC7 | Nuc/Cyt | | 12q13 | H, PL, PA, SM |
| HDAC9 | Nuc/Cyt | 1011 | 7p21-p15 | SM, B |
| Class IIb | | | | |
| HDAC6 | Mainly Cyt | 1215 | Xp11.22-33 | H, L, K, PA |
| HDAC10 | Mainly Cyt | 669 | 22q13.31-33 | L, S, K |
| Class V | | | | |
| HDAC11 | Nuc/Cyt | 347 | 3p25.2 | B, H, SM, K |

*SM = skeletal muscle; B = brain; PL = platelet; L = liver; K = kidney; S = spleen; H = heart; PA = pancreas.
**For References see reviews Dokmanovic et al. Molecular Cancer Research 5: 981-989, 2007

TABLE 2

| No. | Alias | Structure | IC50 on HDAC6 (nM) | IC50 on HDAC1 (nM) | IS50 ratio (1/6) |
|---|---|---|---|---|---|
| 1 | BAHA | 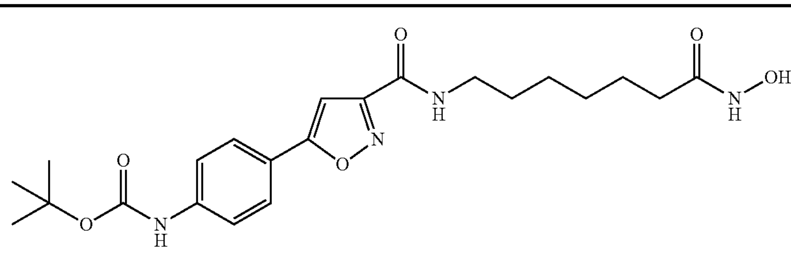 | 6.3 | 53.7 | 8.56 |

TABLE 2-continued

| No. | Alias | Structure | IC50 on HDAC6 (nM) | IC50 on HDAC1 (nM) | IS50 ratio (1/6) |
|---|---|---|---|---|---|
| 2 | tubacin | 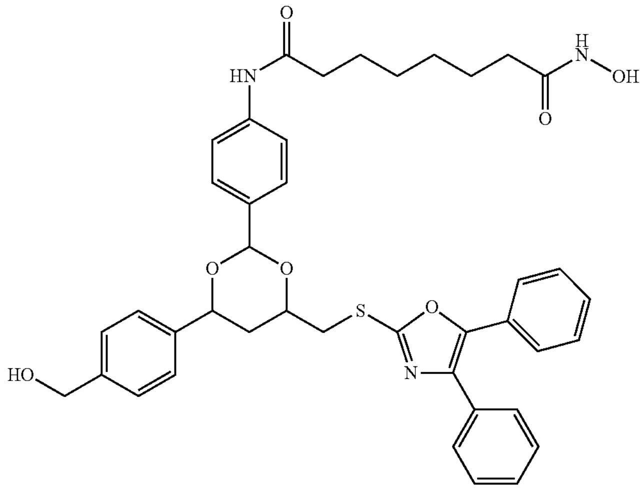 [SMILES: O=C(CCCCCCC(=O)Nc1ccc(C2OC(CSc3nc(-c4ccccc4)c(-c4ccccc4)o3)CC(c3ccc(CO)cc3)O2)cc1)NO] | 21.6 | 82.0 | 3.8 |
| 3 | niltubacin | 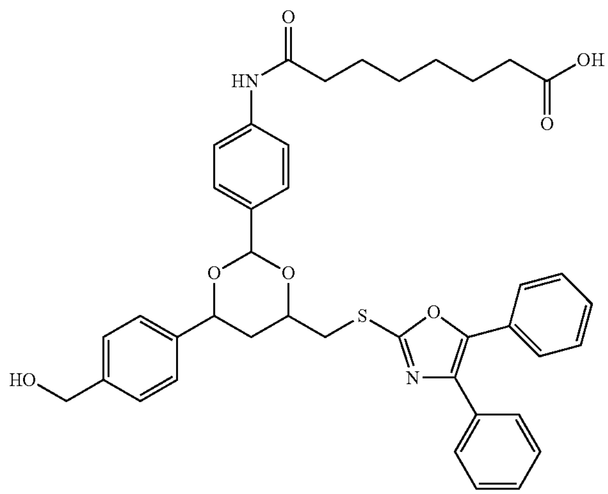 [SMILES: O=C(O)CCCCCCC(=O)Nc1ccc(C2OC(CSc3nc(-c4ccccc4)c(-c4ccccc4)o3)CC(c3ccc(CO)cc3)O2)cc1] | >100 | >100 | NA |
| 4 | SAHA | 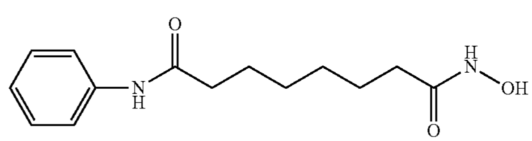 [SMILES: O=C(CCCCCCC(=O)Nc1ccccc1)NO] | 1.31 | 63.3 | 4.8 |

Part B

I. Methods and Materials

Cell Culture.

LNCaP (human prostate cancer), MCF-7 (human breast adenomacarcinoma) and HFS (human foreskin fibroblast) cell lines were obtained from the American Tissue Culture Collection (Manassas, Va.). LNCaP cells were cultured in RPMI medium 1640, MCF-7 in MEM and HFS in F12-K medium, each supplemented with 10% FBS.

Drugs and Chemicals.

Doxorubicin and etoposide were purchased from Sigma. Z-VAD-fmk was purchased from R&D Systems. Tubacin and nil-tubacin were generously provided by Stuart Schreiber, James Bradner and Ralph Mazitschek (Harvard University, Cambridge, Mass.) SAHA was prepared as previously reported (Richon V M, et al. (1996) Proc Natl Acad Sci USA 93(12):5705-5708). Doxorubicin was diluted in sterile distilled water and etoposide, tubacin, nil-tubacin and SAHA were diluted in dimethyl sulfoxide (DMSO) for addition to culture medium. In all studies, an equivalent amount of DMSO without the drug was added to the control culture medium.

Cell Growth and Viability.

To monitor cell growth and viability, cells were seeded in triplicate at $5 \times 10^4$ cells in 1 ml of medium in 24-well plates. The drugs were added at the indicated concentrations 24 h after seeding. Cells were harvested by trypsin digestion at 24 h, 48 h and 72 h following drug additions. Cell number and viability were determined by trypan blue exclusion.

Western Blot Analysis.

$1 \times 10^6$ cells were seeded in a 10 cm diameter cell culture dish and cultured overnight prior to addition of the indicated drugs, washed with PBS, harvested by trypsinisation and lysed in RIPA buffer (50 mM Tris-HCL pH8.0, 120 mM NaCl, 0.5 mM EDTA, 0.5% NP-40). Antibodies used were: HDAC6, HDAC1 and HDAC3 (Santa Cruz Biotechnology), acetylated a-tubulin (Sigma), a-tubulin (Calbiochem), PARP (BD Pharmingen), γH2AX (abcam), H2AX (abcam), phospho-CHK2 (Cell Signaling), DDIT3 (Santa Cruz Biotechnology), GAPDH (Thermo Scientific), Histone H3 (Active Motif). Quantitation of western blots was performed using ImageJ.

RNA Interference.

shRNA lentiviral particles targeting different regions of HDAC6 mRNA, HDAC6 KD1 (HDAC6 knockdown 1) at $1.7 \times 10^7$ TU/ml and HDAC6 KD2 (HDAC6 knockdown 2) at $1.9 \times 10^7$ TU/ml, and a non-targeting 'scramble' shRNA control particles (#SHC002V) at $1.1 \times 10^7$ TU/ml, were purchased from Sigma-Aldrich and transfected according to the manufacturer's instructions using polybrene (Millipore). The 21-nucleotide sequence corresponding to HDAC6 mRNA for HDAC6 KD1 is 5'-CATCCCATCCTGAATATC-CTT-3' and for HDAC6 KD2 is 5'-GCACAGTCTTATG-GATGGCTA-3'. For each shRNA, $5 \times 10^5$ cells were infected at an MOT of 2.

Microarray Analysis.

Alterations in gene expression were evaluated by microarray using the Illumina human cDNA array containing cDNA probes representing the whole genome (10000 genes). $1 \times 10^6$ LNCaP cells were seeded in 10 cm diameter cell culture dishes and incubated for 24 h prior to culture with DMSO (control), 8 mM tubacin, 5 mM SAHA or with 8 mM tubacin and 5 mM SAHA for 2 h, 8 h and 24 h. Triplicate samples were prepared for each drug treatment at each time point. Poly(A)+ mRNA was isolated from cells using Trizol reagent according to manufacturer's protocol (Invitrogen). The data was analyzed using the Bioconductor packages (www.bioconductor.com) for the R statistical system. The output from Beadstudio was processed using the LUMI package. The normalization method used was quantile and the signal levels were log (base 2) transformed. To determine genes that are differentially expressed between the various sample types, the LIMMA package was used.

Quantitative Real-Time PCR.

1 mg of total RNA was reverse-transcribed using the Thermoscript RT-PCR system (Invitrogen) at 52° C. for 1 h. 20 ng of resultant cDNA was used in a Q-PCR reaction using an 7500 Real-Time PCR System (Applied Biosystems) using predesigned primers for DDIT3, DDIT4, Mcm4, Mcm6, Cdt1, Psf2 and GAPDH (Applied Biosystems). Amplification was carried for 40 cycles (95° C. for 15 sec, 60° C. for 1 min). To calculate the efficiency of the PCR reaction, and to assess the sensitivity of each assay, we performed a 6 point standard curve (5, 1.7, 0.56, 0.19, 0.062, and 0.021 ng). Triplicate CT values were averaged, amounts of target were interpolated from the standard curves and normalized to GAPDH (assay Hs99999909_m1).

Cell Cycle Analysis by Flow Cytometry.

$1 \times 10^6$ cells were seeded in a 10 cm diameter cell culture dish and cultured overnight prior to culture with the drugs as indicated for each experiment. Cells were harvested at 24 h culture with the indicated drugs, washed with PBS and fixed in methanol. Cells were then resuspended in a buffer containing 50 mg/ml propidium iodide and 100 mg/ml RNase A. Samples were analysed by flow cytometry using a Becton Dickinson FACSCalibur flow cytometer. Data were collected for 10,000 events and analyzed using FlowJo software.

II. Results

Figure 18A:
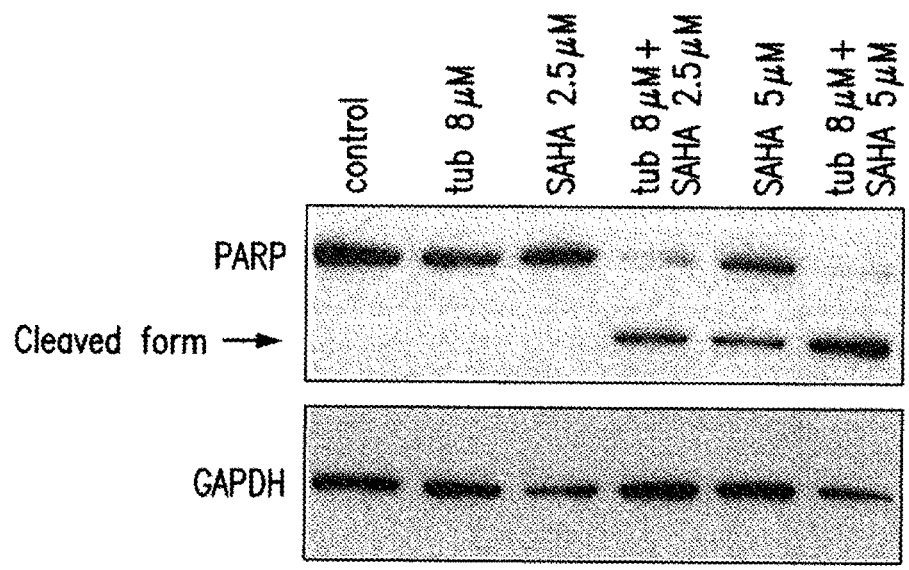
FIGS. 18A-18D Activation of the intrinsic apoptotic pathway is enhanced in transformed cells cultured with tubacin in combination with SAHA or etoposide. (A) Western blot analysis showing PARP degradation in LNCaP cells cultured with DMSO (control), SAHA, tubacin (tub) or simultaneous culture with tubacin and SAHA for 48 h and (B) simultaneous culture of etoposide and tubacin for 48 h. GAPDH is shown as a loading control. (C) Effect of the pan-caspase inhibitor Z-VAD-fmk on cell viability following a 48 h culture with DMSO (control), SAHA, tubacin (tub) or simultaneous addition of SAHA and tubacin and (D) a 48 h culture with DMSO (control), etoposide (eto), tubacin (tub) or simultaneous addition of etoposide and tubacin, with and without Z-VAD-fmk.
Figure 18B:
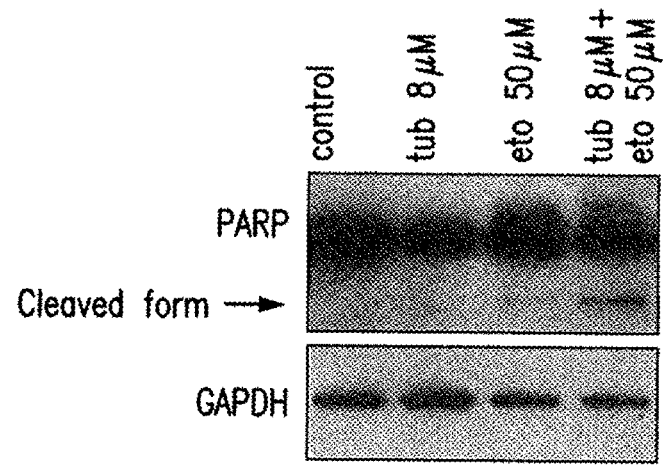
Figure 18C:
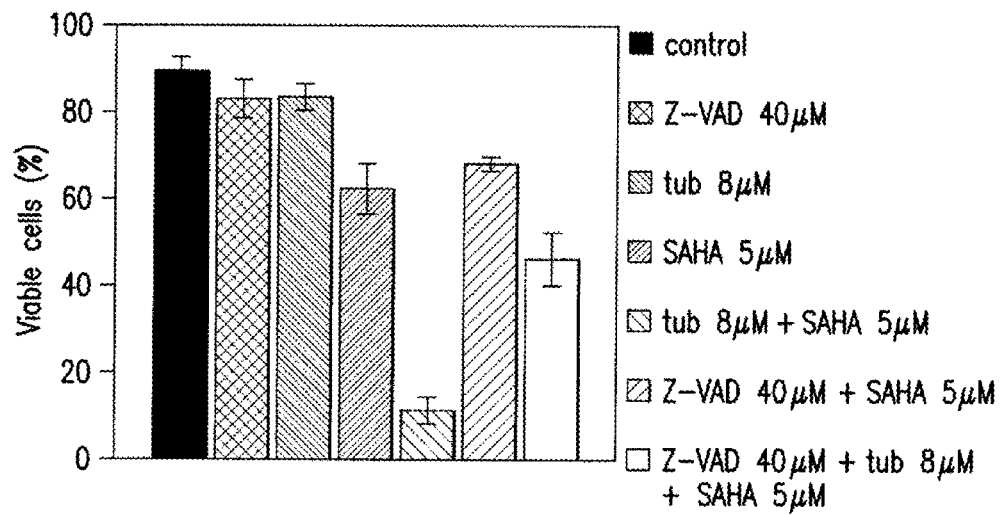
Figure 18D:
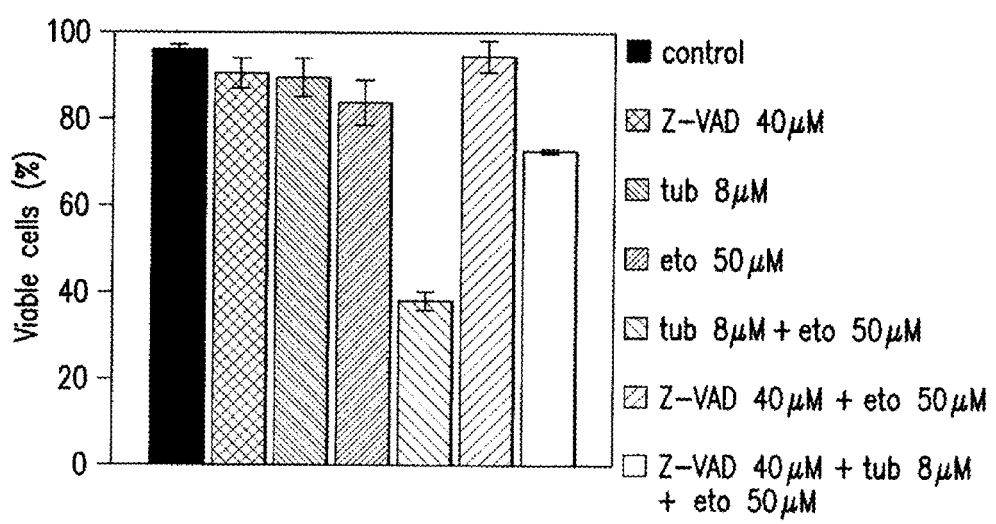

Culture with Tubacin Plus SAHA or Etoposide Enhances Caspase-Dependent Apoptosis in LNCaP Cells To investigate the pathway of cell death in LNCaP cells cultured with the combination of tubacin and SAHA or etoposide, the status of poly(ADP-ribose) polymerase (PARP) and its proteolytic fragments was assayed. PARP is a 116-kDa nuclear protein that is specifically cleaved by caspase-3 into a 85-kDa fragment and serves as a marker of apoptosis (Mullen P (2004) Methods Mol Med 88:171-181). Cells cultured with 5 mM SAHA resulted in PARP cleavage, whilst culture with 2.5 mM SAHA (a concentration that does not induce LNCaP cell death) did not result in PARE cleavage (FIG. 18A). In cells cultured with tubacin in combination with either 2.5 mM or 5 mM SAHA, the level of full-length PARP decreased dramatically, with an increase in cleaved PARP (FIG. 18A). Similarly cells cultured with the combination of tubacin and etoposide induced PARP degradation (FIG. 18B). To further examine caspase-dependent activation in cells cultured with tubacin and SAHA or etoposide, the pan-caspase inhibitor Z-VAD-fmk was added to cultures for 1 h prior to the addition of tubacin plus SAHA or tubacin plus etoposide. The addition of Z-VAD-fmk reduced cell death in LNCaP cells cultured with tubacin in combination with SAHA from 90% to 60% and in combination with etoposide from 65% to 25% (FIGS. 18C and 18D). These findings suggest that cell death induced by the combination of tubacin and SAHA or tubacin and etoposide is, in part, dependent on caspase activation.

Figure 19A:
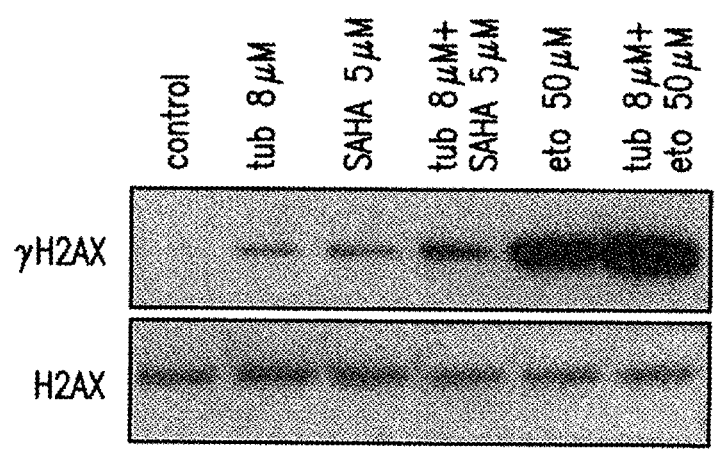
FIGS. 19A-19D Tubacin enhances the accumulation of □H2AX and phospho-Chk2 induced by SAHA or etoposide. (A) Western blot analysis showing accumulation of γH2AX following a 24 h culture with DMSO (control), tubacin (tub), SAHA, etoposide (eto) and the combinations of tubacin with SAHA or etoposide. H2AX is shown as a loading control. (B and C) Quantitation of γH2AX levels of western blots cultured as described in FIG. 19C. The values represent the average of three separate experiments. (D) Western blot analysis of accumulation of phospho-Chk2 following a 24 h culture with DMSO (control), tubacin (tub), SAHA, etoposide (eto) and the combinations of tubacin with SAHA or etoposide.
Figure 19B:
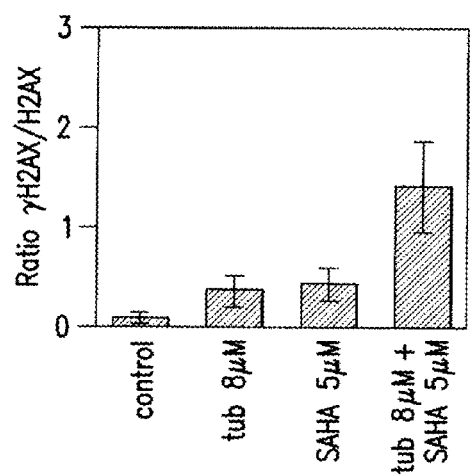
Figure 19C:
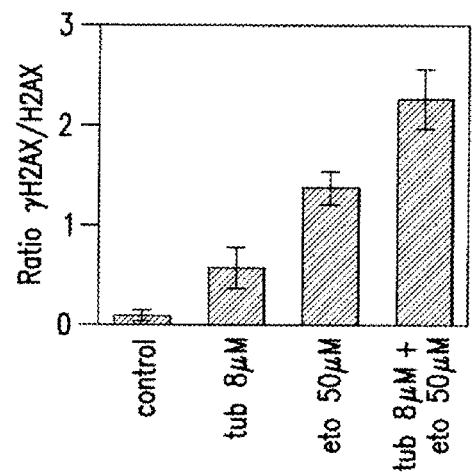

Tubacin Enhances the Accumulation of γH2AX and Phospho-Chk2 Induced by SAHA or Etoposide It was determined whether specific inhibition of HDAC6 with tubacin activated a DNA damage response which may account for tubacin-mediated cell cycle arrest. The accumulation of γH2AX (phosphorylation of histone H2AX), a marker of DNA double-strand breaks (DSBs), increased in LNCaP cells cultured with tubacin or SAHA or etoposide (FIG. 19A). The combination of tubacin with SAHA or with etoposide resulted in a more marked accumulation of γH2AX than in cells cultured with each compound alone (FIG. 19A). Quantitation of γH2AX levels showed an approximately 6-fold increase in gγH2AX when combining tubacin with SAHA compared to SAHA alone (FIG. 19B) and 1.5-fold increase when combining tubacin with etoposide compared to etoposide alone (FIG. 19C).

Figure 19D:
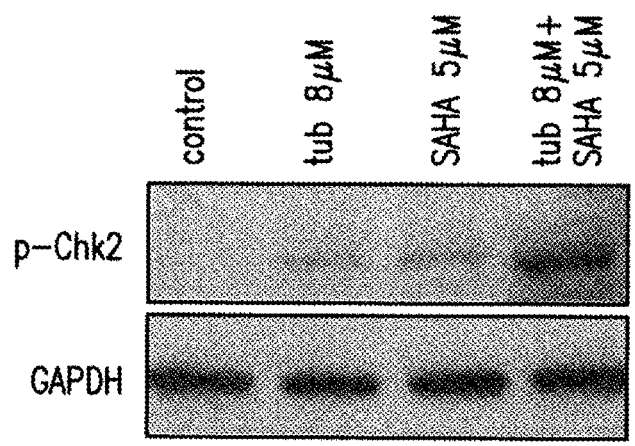
Figure 19D:
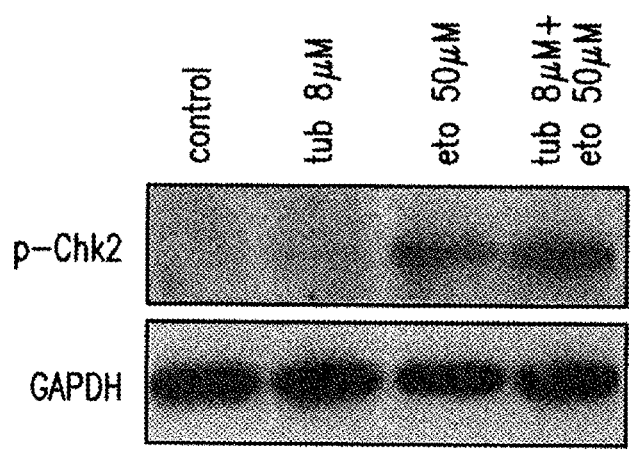

The activation of the checkpoint kinase Chk2 was next assessed. It is phosphorylated on Thr68 in response to DNA damage and has been implicated in both G1 and G2 checkpoint activation (Falck J, et al. (2001) Nature 410(6830): 842-847; Abraham R T (2001) Genes Dev 15(17):2177-2196). Culture with SAHA or etoposide alone resulted in the activation of Chk2 as shown by an increase of phospho-Chk2 (FIG. 19D). The level of phospho-Chk2 was higher when tubacin was cultured in combination with SAHA or etoposide (FIG. 19D). Thus, HDAC6 inhibition can potentiate the DNA damage and checkpoint response induced by SAHA or etoposide.

Figure 20A:
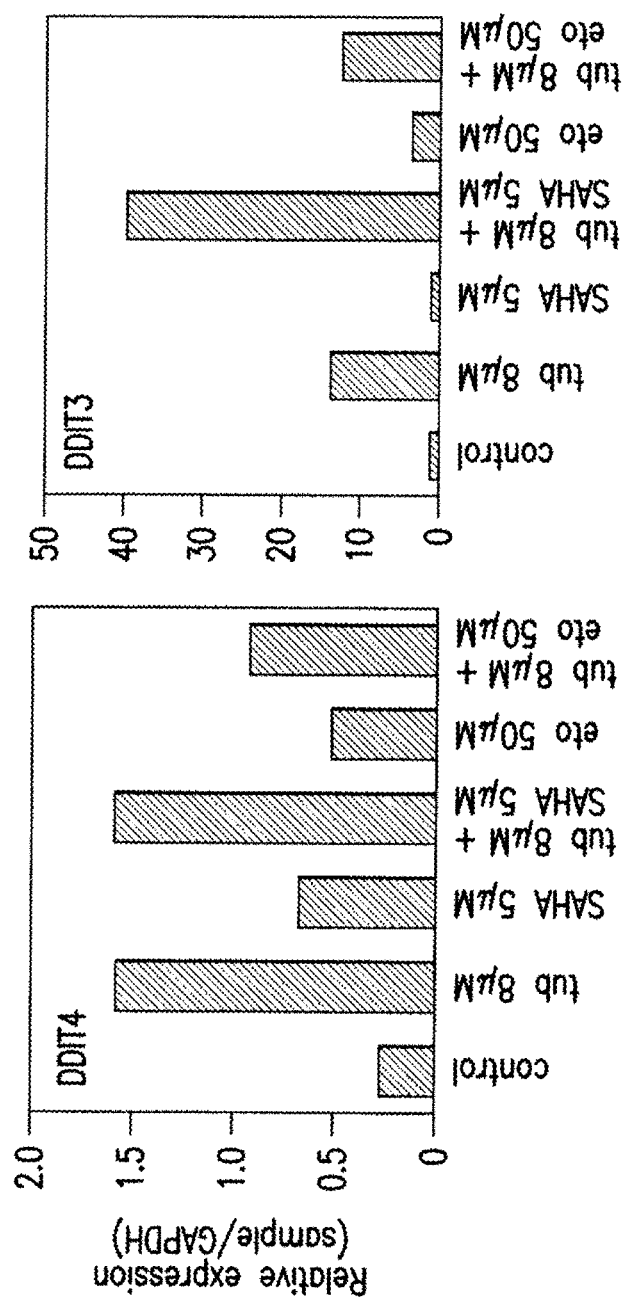
FIGS. 20A-20D Tubacin upregulates DDIT3 and DDIT4, downregulates replication proteins and induces a G1 arrest. (A) Quantitative real-time PCR analysis on LNCaP cells cultured with DMSO (control), tubacin (tub), SAHA, etoposide (eto) and the combinations of tubacin with SAHA or etoposide. Primers utilized were against DDIT3 and DDIT4 (B) Western blot analysis probing with antibodies against acetylated □-tubulin and DDIT3. GAPDH is shown as a loading control. (C) Quantitative real-time PCR analysis on LNCaP cells cultured as described in FIG. 6A. Primers utilized were against Mcm4, Mcm6, Cdt1 and Psf2. (D) Cells cultured as described in FIG. 20A were stained with propidium iodide and assessed by flow cytometry.

Tubacin Upregulates DDIT3 and DDIT4, Downregulates DNA Replication Proteins and Induces a G1 Arrest To further characterise the molecular pathways altered by tubacin, SAHA and the combination of tubacin and SAHA, gene expression profiles were examined following culture of LNCaP cells for 2, 8 and 24 h. In SAHA cultured cells, approximately the same number of genes were up- and downregulated at each time point (Table 3). In culture with tubacin, only one gene, DDIT4 (DNA-damage-inducible transcript 4), also known as RTP801/Dig2/REDD1, was upregulated ≥2-fold at 2 h (Table 4). DDIT4 has been identified in mammalian cells as a gene induced in response to agents that promote DNA damage and ER-stress (Whitney M L, et al. (2009) Biochem Biophys Res Commun 379(2):451-455; Lin L, et al. (2005) Biochemistry 44(10): 3909-3914). The upregulation of DDIT4 was validated by quantitative real-time PCR (FIG. 20A).

Figure 20B:
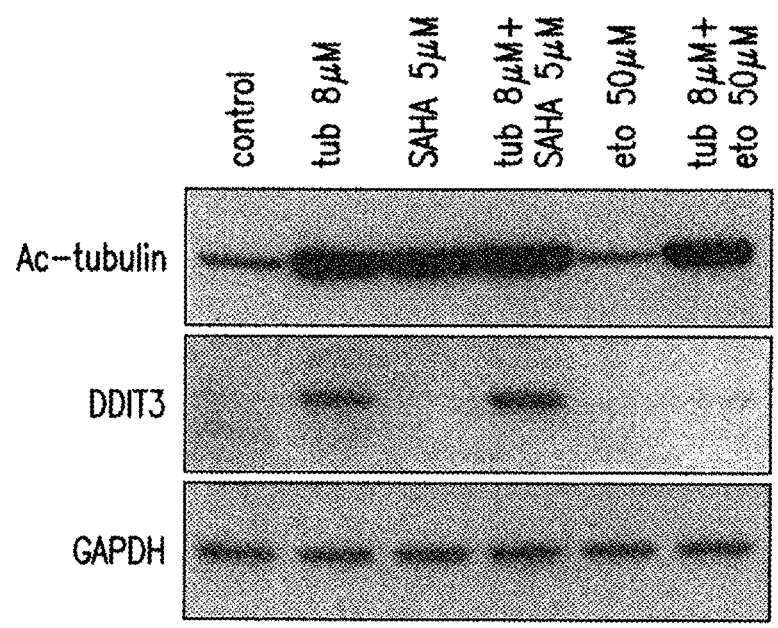

DDIT3 (DNA-damage-inducible transcript 3), also known as CHOP/GADD153, a pro-apoptotic transcription factor upregulated in response to endoplasmic reticulum (ER)-stress (Zinszner H, et al. (1998) Genes Dev 12(7):982-995) was one of six genes upregulated ≥2-fold at 8 h culture of LNCaP with tubacin (Table 4). Culture with SAHA alone did not induce DDIT3 at 8 h and 24 h (Table 4 and FIG. 20A). The combination of tubacin plus SAHA resulted in a 22-fold increase in DDIT3 gene expression compared to a 7-fold increase with tubacin alone at 24 h (Table 4). Increased expression of DDIT3 was confirmed on analysis at the protein level (FIG. 20B).

Figure 20C:
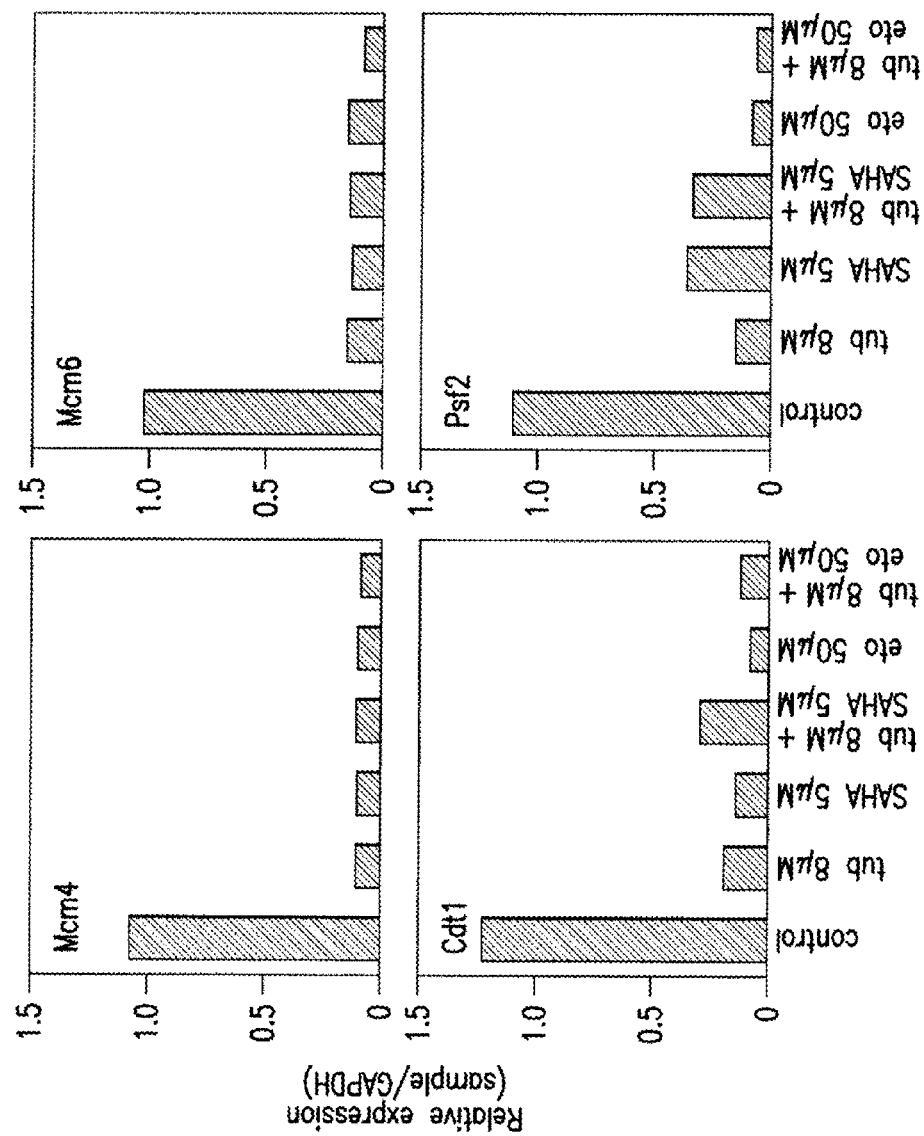
Figure 20D:
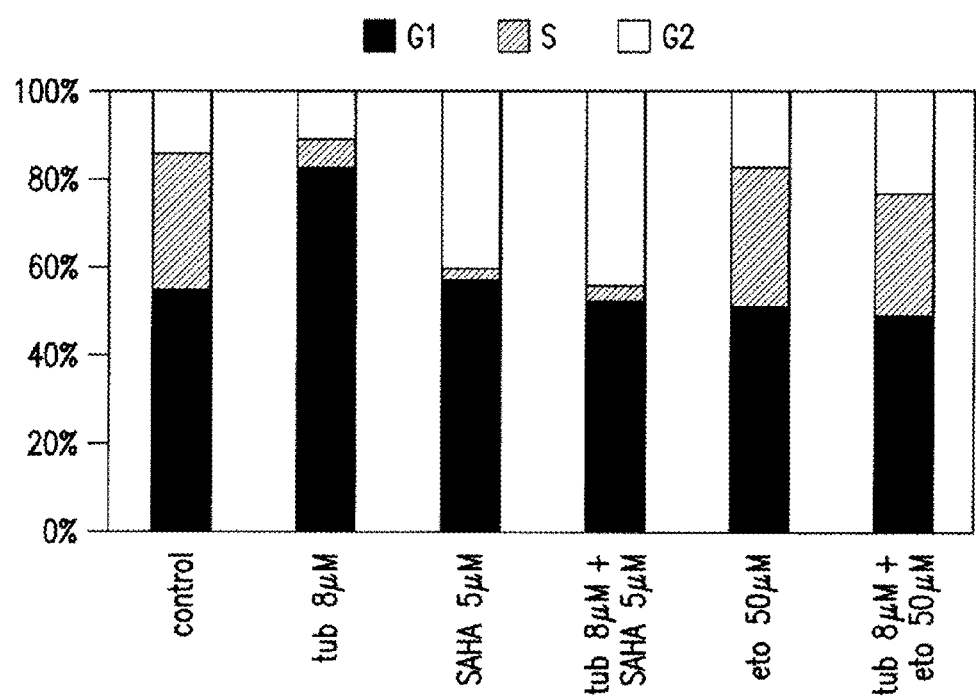

Microarray analysis of LNCaP cells cultured for 24 h with tubacin alone identified 72 genes downregulated ≥2-fold (Table 3), of which approximately 40% were members of the cell cycle machinery [Table 5]. Several genes essential for G1/S transition and replication progression were downregulated in culture with tubacin, SAHA or etoposide alone and in combinations, including Mcm4, Mcm6, Cdt1 and Psf2 (FIG. 20C). LNCaP cells cultured for 24 h with tubacin alone showed an increase in G1 arrest and cells cultured with SAHA showed an increase in both G1 and G2 arrested cells (FIG. 20D). There was a small increase in cells in G1 in cultures with etoposide or etoposide and tubacin (FIG. 20D).

III. Discussion

The specific HDAC6 inhibitor, tubacin, was found to cause an accumulation of γH2AX, a marker of DNA double-strand breaks. The combination of tubacin with SAHA or etoposide, markedly increased the accumulation of γH2AX and phospho-Chk2 in LNCaP cells. These findings suggest that HDAC6 inhibition increased etoposide or SAHA induced accumulation of DNA double-strand breaks which may explain, in part, the chemosensitizing effect of HDAC6 inhibition in transformed cells. Synergistic and additive tumor cell apoptosis has been observed when combining pan-HDAC inhibitors with cytotoxic therapies that induce DNA damage (Karagiannis T C & El-Osta A (2006) Oncogene 25(28):3885-3893; Kim M S, et al. (2003) Cancer Res 63(21):7291-7300; Marchion D C, at al. (2004) J Cell Biochem 92(2):223-237).

Enhanced DNA damage observed in these combination therapies has been attributed to the induction of histone hyperacetylation by the HDAC inhibitor resulting in a more open chromatin structure making DNA more susceptible to damage by various toxic agents (Martinez-Lopez W, et al. (2001) Chromosome Res 9(1); 69-75). Additionally, pan-HDAC inhibitors such as SAHA can suppress DNA repair proteins in transformed cells resulting in failure to repair DNA damage (Zhang Y, et al. (2007) Radiat Res 168(1): 115-124; Adimoolam S, et al. (2007) Proc Natl Acad Sci USA 104(49):19482-19487; Munshi A, et al. (2005) Clin Cancer Res 11(13):4912-4922). HDAC6-specific inhibition does not cause accumulation of acetylated histones.

Target proteins of HDAC6 include the chaperone protein HSP90 (Bali P, et al. (2005) J Biol Chem 280(29):26729-26734; Kovacs J J, et al. (2005) Mol Cell 18(5):601-607). Acetylation of Hsp90 impairs its chaperone function and exposes its client proteins, eg. Akt, to degradation which is associated with activation of the intrinsic apoptotic pathway.

In this study, it was found that tubacin markedly enhanced SAHA and etoposide induced transformed cell apoptosis as evidenced by both increased PARP cleavage and caspase dependent cell death. Microarray analysis of LNCaP cells cultured with SAHA found downregulation of a number of genes involved in DNA damage and repair [Table 6] This suggests that tubacin induced accumulation of DNA breaks in LNCaP cells cultured with SAHA may also result from an impaired capacity to repair DNA breaks. Several proteins involved in the DNA damage repair pathway have been identified as targets of lysine acetylation (Choudhary C, et al. (2009) Science 325(5942):834-840). Acetylation of DNA repair proteins has been shown to alter their activity (Chen C S, et al. (2007) Cancer Res 67(11):5318-5327; Sun Y, et al. (2007) Mol Cell Biol 27(24):8502-8509).

HDAC6 plays an important role in the removal of misfolded and damaged proteins through its ability to recruit polyubiquitinated proteins to dynein motors and transporting them to aggresomes (Kawaguchi Y, et al. (2003) Cell 115(6):727-738; Boyault C, et al. (2006) EMBO J. 25(14): 3357-3366). HDAC6 inhibition was found to induce the expression of DDIT3, a transcription factor that is upregulated in response to ER-stress and regulates the expression of target genes whose products mediate ER-stress-induced apoptosis (Zinszner H, et al. (1998) Genes Dev 12(7):982-995). LNCaP cells cultured with tubacin plus SAHA enhanced DDIT3 induction which may explain, in part, the chemosensitizing effect of HDAC6 inhibition in combination with a pan-HDAC inhibitor in transformed cells.

It is difficult to accurately establish a correspondence between an effective concentration of agents in transformed cell based assays and therapeutically effective plasma concentrations. The present findings suggest that at concentrations of SAHA, doxorubicin or etoposide that are clinically attainable and tolerated (Rahman A, et al. (1986) Cancer Res 46(5):2295-2299; Hande K R, et al. (1984) Cancer Res 44(1):379-382; Kelly W K, et al. (2005) J Clin Oncol 23(17):3923-3931), HDAC6 selective inhibitors could enhance the therapeutic efficacy of these agents. Selective inhibition of HDAC6 is an attractive target in enhancing the efficacy of cytotoxic anti-cancer drugs.

IV. Synopsis

Transformed cells cultured with tubacin in combination with SAHA or etoposide is more potent than either drug alone in activating the intrinsic apoptotic pathway as evidenced by an increase in PARP cleavage and partial inhibition of this effect by the pan-caspase inhibitor, Z-VAD-fmk. It was found that HDAC6 inhibition with tubacin induces the accumulation of γH2AX, a marker of DNA double-strand breaks. Tubacin enhances DNA damage induced by etoposide or SAHA as indicated by increased accumulation of γH2AX and activation of the checkpoint kinase, Chk2. Tubacin induces the expression of DDIT3 (CHOP/GADD153), a pro-apoptotic transcription factor upregulated in response to endoplasmic reticulum stress. DDIT3 induction is further increased when tubacin is combined with SAHA. These findings point to novel mechanisms by which HDAC6-specific inhibitors can enhance the efficacy of certain anti-cancer agents and the importance of HDAC6 as a target for cancer therapy.

TABLE 3

| Treatment | Total gene number | Upregulated genes | Downregulated genes |
|---|---|---|---|
| SAHA 2 h | 37 | 21 | 16 |
| SAHA 8 h | 628 | 326 | 302 |
| SAHA 24 h | 1951 | 962 | 989 |

TABLE 3-continued

| Treatment | Total gene number | Upregulated genes | Downregulated genes |
|---|---|---|---|
| tubacin 2 h | 1 | 1 | 0 |
| tubacin 8 h | 7 | 6 | 1 |
| tubacin 24 h | 225 | 153 | 72 |
| tubacin + SAHA 2 h | 29 | 19 | 10 |
| tubacin + SAHA 8 h | 694 | 340 | 354 |
| tubacin + SAHA 24 h | 2149 | 1097 | 1052 |

TABLE 4

| Gene symbol | Gene name | tubacin 2 h | tubacin 8 h | tubacin 24 h | SAHA 2 h | SAHA 8 h | SAHA 24 h | tubacin + SAHA 2 h | tubacin + SAHA 8 h | tubac + SAI 24 b |
|---|---|---|---|---|---|---|---|---|---|---|
| DDIT3 | *Homo sapiens* DNA-damage-inducible transcript 3 (DDIT3) (RTP801/Dig2/REDD1) | * | 2.22 | 7.04 | 2.18 | * | * | 2.1 | 2.5 | 22.3 |
| DDIT4 | *Homo sapiens* DNA-damage-inducible transcript 4 (DDIT4) (CHOP/GADD153) | 2.01 | 5.54 | 6.8 | * | 5.36 | 3.81 | * | 6.4 | 7.09 |

* No detectable change of ≥2-fold

TABLE 5

| Gene symbol | Gene name | Fold change |
|---|---|---|
| MCM4 | *Homo sapiens* minichromosome maintenance complex component 4 (MCM4), transcript variant 1, mRNA. | −3.13 |
| CDCA7 | *Homo sapiens* cell division cycle associated 7 (CDCA7), transcript variant 1, mRNA. | −3.03 |
| GINS2 | *Homo sapiens* GINS complex subunit 2 (Psf2 homolog) (GINS2), mRNA. | −2.94 |
| UHRF1 | *Homo sapiens* ubiquitin-like with PHD and ring finger domains 1 (UHRF1), transcript variant 1, mRNA. | −2.92 |
| LFNG | *Homo sapiens* LFNG O-fucosylpeptide 3-beta-N-acetylglucosaminyltransferase (LFNG), transcript variant 1, mRNA. | −2.74 |
| MYB | *Homo sapiens* v-myb myeloblastosis viral oncogene homolog (avian) (MYB), transcript variant 2, mRNA. | −2.68 |
| LAMA1 | *Homo sapiens* laminin, alpha 1 (LAMA1), mRNA. | −2.66 |
| MCM10 | *Homo sapiens* minichromosome maintenance complex component 10 (MCM10), transcript variant 2, mRNA. | −2.66 |
| CDT1 | *Homo sapiens* chromatin licensing and DNA replication factor 1 (CDT1), mRNA. | −2.63 |
| TYMS | *Homo sapiens* thymidylate synthetase (TYMS), mRNA. | −2.61 |
| NKX3-1 | *Homo sapiens* NK3 homeobox 1 (NKX3-1), mRNA. | −2.56 |
| NUDT1 | *Homo sapiens* nudix (nucleoside diphosphate linked moiety X)-type motif 1 (NUDT1), transcript variant 2A, mRNA. | −2.56 |
| MCM6 | *Homo sapiens* minichromosome maintenance complex component 6 (MCM6), mRNA. | −2.55 |
| FKBP5 | *Homo sapiens* FK506 binding protein 5 (FKBP5), mRNA. | −2.54 |
| GEMIN4 | *Homo sapiens* gem (nuclear organelle) associated protein 4 (GEMIN4), mRNA. | −2.49 |
| MCM7 | *Homo sapiens* minichromosome maintenance complex component 7 (MCM7), transcript variant 2, mRNA. | −2.48 |
| STRA13 | *Homo sapiens* stimulated by retinoic acid 13 homolog (mouse) (STRA13), mRNA. | −2.41 |
| ASF1B | *Homo sapiens* ASF1 anti-silencing function 1 homolog B (*S. cerevisiae*) (ASF1B), mRNA. | −2.41 |
| LRRC45 | *Homo sapiens* leucine rich repeat containing 45 (LRRC45), mRNA. | −2.4 |
| TUBA3D | *Homo sapiens* tubulin, alpha 3d (TUBA3D), mRNA. | −2.39 |
| SNRPA1 | *Homo sapiens* small nuclear ribonucleoprotein polypeptide A' (SNRPA1), mRNA. | −2.37 |
| LOC399942 | PREDICTED: *Homo sapiens* similar to Tubulin alpha-2 chain (Alpha-tubulin 2), transcript variant 5 (LOC399942), mRNA. | −2.35 |
| SLC25A19 | *Homo sapiens* solute carrier family 25 (mitochondrial thiamine pyrophosphate carrier), member 19 (SLC25A19), nuclear gene encoding mitochondrial protein, mRNA. | −2.33 |
| MCM5 | *Homo sapiens* minichromosome maintenance complex component 5 (MCM5), mRNA. | −2.31 |
| EXO1 | *Homo sapiens* exonuclease 1 (EXO1), transcript variant 1, mRNA. | −2.3 |
| UCHL5IP | *Homo sapiens* UCHL5 interacting protein (UCHL5IP), transcript variant 1, mRNA. | −2.3 |
| PCNA | *Homo sapiens* proliferating cell nuclear antigen (PCNA), transcript variant 2, mRNA. | −2.26 |
| CDK2 | *Homo sapiens* cyclin-dependent kinase 2 (CDK2), transcript variant 1, mRNA. | −2.25 |
| ADH1A | *Homo sapiens* alcohol dehydrogenase 1A (class I), alpha polypeptide (ADH1A), mRNA. | −2.23 |
| CDCA5 | *Homo sapiens* cell division cycle associated 5 (CDCA5), mRNA. | −2.23 |
| CDC25A | *Homo sapiens* cell division cycle 25 homolog A (*S. pombe*) (CDC25A), transcript variant 1, mRNA, | −2.21 |
| ATAD2 | *Homo sapiens* ATPase family, AAA domain containing 2 (ATAD2), mRNA. | −2.21 |
| MCM4 | *Homo sapiens* minichromosome maintenance complex component 4 (MCM4), transcript variant 2, mRNA. | −2.21 |
| LYAR | *Homo sapiens* Ly1 antibody reactive homolog (mouse) (LYAR), mRNA. | −2.19 |
| LOC647000 | PREDICTED: *Homo sapiens* similar to tubulin, beta 5 (LOC647000), mRNA. | −2.16 |
| RAD54L | *Homo sapiens* RAD54-like (*S. cerevisiae*) (RAD54L), mRNA. | −2.14 |
| MCM7 | *Homo sapiens* minichromosome maintenance complex component 7 (MCM7), transcript variant 1, mRNA. | −2.14 |
| NPTX2 | *Homo sapiens* neuronal pentraxin II (NPTX2), mRNA. | −2.11 |
| RDH13 | *Homo sapiens* retinol dehydrogenase 13 (all-trans/9-cis) (RDH13), mRNA. | −2.11 |
| CCNA2 | *Homo sapiens* cyclin A2 (CCNA2), mRNA. | −2.11 |
| C20orf72 | *Homo sapiens* chromosome 20 open reading frame 72 (C20orf72), mRNA. | −2.11 |
| XRCC3 | *Homo sapiens* X-ray repair complementing defective repair in Chinese hamster cells 3 (XRCC3), transcript variant 3, mRNA. | −2.11 |

TABLE 5-continued

| Gene symbol | Gene name | Fold change |
|---|---|---|
| UNG | Homo sapiens uracil-DNA glycosylase (UNG), transcript variant 1, mRNA. | −2.1 |
| BIRC5 | Homo sapiens baculoviral IAP repeat-containing 5 (BIRC5), transcript variant 1, mRNA. | −2.1 |
| FAM83D | Homo sapiens family with sequence similarity 83, member D (FAM83D), mRNA. | −2.1 |
| CDC45L | Homo sapiens CDC45 cell division cycle 45-like (S. cerevisiae) (CDC45L), mRNA. | −2.09 |
| PAQR4 | Homo sapiens progestin and adipoQ receptor family member IV (PAQR4), mRNA. | −2.09 |
| FEN1 | Homo sapiens flap structure-specific endonuclease 1 (FEN1), mRNA. | −2.09 |
| BCL2L12 | Homo sapiens BCL2-like 12 (proline rich) (BCL2L12), transcript variant 3, mRNA. | −2.09 |
| MCM2 | Homo sapiens minichromosome maintenance complex component 2 (MCM2), mRNA. | −2.08 |
| XTP3TPA | Homo sapiens XTP3-transactivated protein A (XTP3TPA), mRNA, | −2.07 |
| SLC29A1 | Homo sapiens solute carrier family 29 (nucleoside transporters), member 1 (SLC29A1), nuclear gene encoding mitochondrial protein, transcript variant 4, mRNA. | −2.06 |
| ARHGDIA | Homo sapiens Rho GDP dissociation inhibitor (GDI) alpha (ARHGDIA), mRNA. | −2.06 |
| RRM2 | Homo sapiens ribonucleotide reductase M2 polypeptide (RRM2), mRNA. | −2.06 |
| LOC652595 | PREDICTED: Homo sapiens similar to U2 small nuclear ribonucleoprotein A (U2 snRNP-A) (LOC652595), mRNA. | −2.06 |
| MCM10 | Homo sapiens minichromosome maintenance complex component 10 (MCM10), transcript variant 2, mRNA. | −2.05 |
| YWHAH | Homo sapiens tyrosine 3-monooxygenase/tryptophan 5-monooxygenase activation protein, eta polypeptide (YWHAH), mRNA. | −2.04 |
| CCNF | Homo sapiens cyclin F (CCNF), mRNA. | −2.04 |
| ADH1C | Homo sapiens alcohol dehydrogenase 1C (class I), gamma polypeptide (ADH1C), mRNA. | −2.04 |
| IRX3 | Homo sapiens iroquois homeobox 3 (IRX3), mRNA. | −2.04 |
| E2F2 | Homo sapiens E2F transcription factor 2 (E2F2), mRNA. | −2.03 |
| FN3KRP | Homo sapiens fructosamine-3-kinase-related protein (FN3KRP), mRNA. | −2.03 |
| SLC29A1 | Homo sapiens solute carrier family 29 (nucleoside transporters), member 1 (SLC29A1), nuclear gene encoding mitochondrial protein, transcript variant 4, mRNA. | −2.03 |
| CCNE2 | Homo sapiens cyclin E2 (CCNE2), transcript variant 2, mRNA. | −2.03 |
| SUV39H1 | Homo sapiens suppressor of variegation 3-9 homolog 1 (Drosophila) (SUV39H1), mRNA. | −2.02 |
| DNMT1 | Homo sapiens DNA (cytosine-5-)-methyltransferase 1 (DNMT1), mRNA. | −2.01 |
| C11orf82 | Homo sapiens chromosome 11 open reading frame 82 (C11orf82), mRNA. | −2.01 |
| SLBP | Homo sapiens stem-loop binding protein (SLBP), mRNA. | −2.01 |
| NOL5A | Homo sapiens nucleolar protein 5A (56 kDa with KKE/D repeat) (NOL5A), mRNA. | −2.01 |
| NP | Homo sapiens nucleoside phosphorylase (NP), mRNA. | −2.01 |
| GAL | Homo sapiens galanin prepropeptide (GAL), mRNA. | −2.01 |
| LOC642031 | PREDICTED: Homo sapiens hypothetical protein LOC642031 (LOC642031), mRNA. | −2 |

TABLE 6

| Gene symbol | Gene name | Fold change |
|---|---|---|
| BIRC5 | Homo sapiens baculoviral IAP repeat-containing 5 (BJRC5), transcript variant 1, mRNA. | −5.18 |
| BRCA1 | Homo sapiens breast cancer 1, early onset (BRCA1), transcript variant BRCA1-delta14-17, mRNA. | −2.15 |
| CCND1 | Homo sapiens cyclin D1 (CCND1), mRNA. | −10.06 |
| CDC25A | Homo sapiens cell division cycle 25 homolog A (S. pombe) (CDC25A), transcript variant 1, mRNA. | −4.5 |
| CDC25C | Homo sapiens cell division cycle 25 homolog C (S. pombe) (CDC25C), transcript variant 1, mRNA. | −2.18 |
| CHEK1 | Homo sapiens CHK1 checkpoint homolog (S. pombe) (CHEK1), mRNA. | −4.51 |
| CHEK2 | Homo sapiens CHK2 checkpoint homolog (S. pombe) (CHEK2), transcript variant 1, mRNA. | −2 |
| E2F2 | Homo sapiens E2F transcription factor 2 (E2F2), mRNA. | −3.05 |
| FANCG | Homo sapiens Fanconi anemia, complementation group G (FANCG), mRNA. | −2.43 |
| FOXM1 | Homo sapiens forkhead box M1 (FOXM1), transcript variant 2, mRNA. | −4.11 |
| H2AFX | Homo sapiens H2A histone family, member X (H2AFX), mRNA. | −3.24 |
| HIPK2 | Homo sapiens homeodomain interacting protein kinase 2 (HIPK2), mRNA. | −2.5 |
| MYB | Homo sapiens v-myb myeloblastosis viral oncogene homolog (avian) (MYB), transcript variant 2, mRNA. | −2.61 |
| MYC | Homo sapiens v-myc myelocytomatosis viral oncogene homolog (avian) (MYC), mRNA. | −4.26 |
| NME1 | Homo sapiens non-metastatic cells 1, protein (NM23A) expressed in (NME1), transcript variant 1, mRNA. | −3.12 |
| NUPR1 | Homo sapiens nuclear protein 1 (NUPR1), transcript variant 1, mRNA. | −3.65 |
| PBK | Homo sapiens PDZ binding kinase (PBK), mRNA. | −2.29 |
| PHLDA3 | Homo sapiens pleckstrin homology-like domain, family A, member 3 (PHLDA3), mRNA, | −2.12 |
| PLK1 | Homo sapiens polo-like kinase 1 (Drosophila) (PLK1), mRNA. | −2.13 |
| RAD54L | Homo sapiens RAD54-like (S. cerevisiae) (RAD54L), mRNA. | −2.89 |
| SFRS2 | Homo sapiens splicing factor, arginine/serine-rich 2 (SFRS2), mRNA. | −2.15 |
| TOP2A | Homo sapiens topoisomerase (DNA) II alpha 170 kDa (TOP2A), mRNA. | −5.13 |
| TOPBP1 | Homo sapiens topoisomerase (DNA) II binding protein 1 (TOPBP1), mRNA. | −2.1 |
| TP53 | Homo sapiens tumor protein p53 (TP53), mRNA. | −2.24 |
| XRCC3 | Homo sapiens X-ray repair complementing defective repair in Chinese hamster cells 3 (XRCC3), transcript variant 3, mRNA. | −2.65 |

What is claimed is:

1. A method for inducing cell death of a cancer cell, comprising concurrently contacting the cell with (i) a histone deacetylase (HDAC) 6-selective inhibitor selected from the group consisting of tubacin and BAHA, and (ii) a cytotoxic agent selected from the group consisting of suberoylanilide hydroxamic acid (SAHA), doxorubicin, and etoposide, wherein the amounts of the HDAC 6-selective inhibitor and cytotoxic agent, when concurrently contacted with the cell, are effective to increase sensitivity of the cancer cell to the cell death induced by the cytotoxic agent, wherein the cancer cell is a breast cancer cell or a prostate cancer cell.

2. The method of claim 1, wherein the HDAC 6-selective inhibitor is tubacin.

3. The method of claim 1, wherein the HDAC 6-selective inhibitor is BAHA.

4. The method of claim 1, wherein the cytotoxic agent is SAHA.

5. The method of claim 1, wherein the cytotoxic agent is doxorubicin.

6. The method of claim 1, wherein the cytotoxic agent is etoposide.

7. A method for treating a subject afflicted with cancer, comprising concurrently administering to the subject one of the following combinations of agents selected from the group consisting of: (i) tubacin and SAHA; (ii) tubacin and doxorubicin; (iii) tubacin and etoposide; (iv) BAHA and SAHA; (v) BAHA and doxorubicin; and (vi) BAHA and etoposide, wherein the amounts of each agent in each combination, when concurrently administered, are therapeutically effective to increase sensitivity of cancer cells to SAHA-, doxorubicin-, or etoposide-induced cell death.

8. The method of claim 7, wherein the subject is human.

9. The method of claim 7, wherein the combination of agents is tubacin and SAHA.

10. The method of claim 7, wherein the combination of agents is tubacin and doxorubicin.

11. The method of claim 7, wherein the combination of agents is tubacin and etoposide.

12. The method of claim 7, wherein the combination of agents is BAHA and SAHA.

13. The method of claim 7, wherein the combination of agents is BAHA and doxorubicin.

14. The method of claim 7, wherein the combination of agents is BAHA and etoposide.

* * * * *